(12) United States Patent
Liu

(10) Patent No.: US 9,453,264 B2
(45) Date of Patent: *Sep. 27, 2016

(54) DIRECT QUANTITATIVE PCR ABSENT MINOR GROOVE BINDERS

(71) Applicant: LIFE TECHNOLOGIES CORPORATION, Carlsbad, CA (US)

(72) Inventor: Jason Yingjie Liu, Foster City, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/736,922

(22) Filed: Jun. 11, 2015

(65) Prior Publication Data

US 2015/0376721 A1    Dec. 31, 2015

Related U.S. Application Data

(63) Continuation of application No. 14/318,925, filed on Jun. 30, 2014, now Pat. No. 9,212,388.

(51) Int. Cl.
*C12Q 1/68* (2006.01)
*C12Q 1/70* (2006.01)

(52) U.S. Cl.
CPC .......... *C12Q 1/701* (2013.01); *C12Q 1/682* (2013.01); *C12Q 1/686* (2013.01); *C12Q 1/6816* (2013.01); *C12Q 1/6851* (2013.01)

(58) Field of Classification Search
None
See application file for complete search history.

(56) References Cited

U.S. PATENT DOCUMENTS

2005/0260618 A1   11/2005 Cullor et al.
2007/0269822 A1   11/2007 Cullor et al.
2009/0286251 A1*  11/2009 Xu ..................... C12Q 1/6844
                                                              435/6.18

OTHER PUBLICATIONS

Nozawa et al. (Real-Time PCR Assay Using Specimens on Filter Disks as a Template for Detection of Cytomegalovirus in Urine, Journal of Clinical Microbiology, Apr. 2007, p. 1305-1307).*
Muthukrishnan et al. (Evaluation of FTA® cards as a laboratory and field sampling device for the detection of foot-and-mouth disease virus and serotyping by RT-PCR and real-time RT-PCR, Journal of Virological Methods 151 (2008) 311-316, Jun. 26, 2008).*
Shaw et al. (Implementation of a one-step real-time RT-PCR protocol for diagnosis of foot-and-mouth disease, Journal of Virological Methods 143 (2007) 81-85).*

Gault, E. et al., "Quantification of Human Cytomegalovirus DNA by Real-Time PCR", *Journal of Clinical Microbiology,* vol. 39 (2), Feb. 2001, 772-775.
Life Technologies, "AmpFlstr Identifiler Direct PCR Amplification Kit", *User Guide,* Publication Part No. 4415125 Rev. H, Jun. 2012, 1-131.
Life Technologies, , "Custom TaqMan MGB, Tamra, or QSY Probes", 2014, 2 pages.
Milne, E. et al., "Buccal DNA Collection: Comparison of Buccal Swabs with FTA Cards", *Cancer Epidemiol Biomarkers Prev,* vol. 15 (4), Apr. 2006, 816-819.
Muthukrishnan, M. et al., "Evaluation of FTA cards as a laboratory and field sampling device for the detection of foot-and-mouth disease virus and serotyping by RT-PCR and real-time RT-PCR", *Journal of Virological Methods,* vol. 51, Jun. 26, 2008, 311-316.
Nozawa, N. et al., "Real-Time PCR Assay Using Specimens on Filter Disks as a Template for Detection of Cytomegalovirus in Urine", *Journal of Clinical Microbiology,* vol. 45, No. 4, Apr. 2007, 1305-1307.
Ogawa, H. et al., "Etiology of Severe Sensorineural Hearing Loss in Children: Independent Impact of Congenital Cytomegalovirus Infection and GJB2 Mutations", *The Journal of Infectious Diseases,* vol. 195, Feb. 6, 2007, 782-788.
Qiagen, "QuantiTect Probe PCR Handbook", May 2011, 1-28.
Shaw, A. et al., "Implementation of a one-step real-time RT-PCR protocol for diagnosis of foot-and-mouth disease", *Journal of Virological Methods,* vol. 143, Mar. 29, 2007, 81-85.
McCord, B. "DNA Quantitation by Real Time PCE: Advanced Issues" International Forensic Research Institute, Florida International University, Department of Chemistry, 2011, pp. 1-90.
Zhong, X., et al. Direct Quanfitication of Fetal Cells in Maternal Blood by Real-Time PCT, Prental Diagnosis, vol. 26, 2006, pp. 850-854.
Applied Biosystems, "Quantifiler Duo DNA Quantification Kit User's Manual" 2012, pp. 1-20; retrieved Sep. 8, 2015 from: https://www3.appliedbiosystems.com/cms/groups/applied_markets_support/documents/generaldocuments/cms_049050.pdf.
Applied Biosystems, "Quantifiler HP and Quantifiler TrioDNA Quantification Kits User Guide" 2014 pp. 1-15; retrieved Sep. 8, 2015 from: http://tools.thermofisher.com/content/sfs/manuals/4485354.pdf.
Life Technologies, "Quantifiler HP and Quantifiler Trio DNA Quantification Kits Product Bulletin" 2014 pp. 1-13; table 1; retrieved Sep. 8, 2015 from: http://resource.lifetechnologies.com/lib/WE218399/Product-Bulletin-Quantifiler-HP-Trio.pdf.
Lukka, M. et al. "Triallelic patterns in STR loci used for paternity analysis: Evidence for a duplication in chromosome 2 containing the TPOX STR locus," Forensic Science International, vol. 164, No. 1, 2006, pp. 3-9.
Liu, J., "Direct qPCR Quantification using the Quantifiler Trio DNA Quantification Kit," Forensic Science International: Genetics, vol. 13, 2014, pp. 10-19.

* cited by examiner

*Primary Examiner* — Aaron Priest

(57) ABSTRACT

Disclosed herein are methods, compositions and kits for the quantification of a nucleic acid target present on a solid support. This entails quantitative real-time polymerase chain reaction wherein minor groove binders are excluded.

9 Claims, 16 Drawing Sheets

DIRECT QUANTITATIVE PCR ABSENT MINOR GROOVE BINDERS

CROSS-REFERENCE TO RELATED APPLICATION(S)

This application is a continuation of U.S. patent application Ser. No. 14/318,925 filed Jun. 30, 2014, which is incorporated herein by reference in its entirety.

BACKGROUND

Nucleic acid can be quantified using Polymerase Chain Reaction (PCR) by the detection of amplification products present at the end of PCR, endpoint quantitative PCR, or during PCR, quantitative real-time PCR (qrtPCR). In qrtPCR, fluorescent dyes are generally used to detect PCR products during thermal cycling. This allows quantification of the template to be based on the intensity of the fluorescent signal during the exponential phase of amplification; before limiting reagents or the inactivation of the polymerase have started to have an effect on the efficiency of PCR amplification.

Specialized instruments are used for qrtPCR assays. These qrtPCR instruments couple the thermal cycling function of PCR machines with a fluorimeter. This combination of a thermal cycling function and a fluorimeter allows for in-tube, real-time analysis.

qrtPCR is conducted by placing a reaction tube(s) in a qrtPCR instrument and subjecting the reaction tube(s) to thermal cycling. During each thermal cycling round, the reaction tube is illuminated with light and fluorescence emanating from a reaction tube is collected by the fluorimeter. Because the accuracy of qrtPCR depends on the measurement of fluorescent emissions factors that interfere or interrupt the optical pathway are minimized.

The dominant thinking has been that opaque materials within a qrtPCR reaction tube would mask fluorescent signals and therefore should be excluded. Counter to this, a few groups have now reported qrtPCR assays wherein filter paper is present in the reaction tube during qrtPCR. Significantly each of these groups has reported that the presence of filter paper increases background fluorescence.

Thus, prior to the instant disclosure a need in the art existed for a simplified qrtPCR assay, wherein the background fluorescent observed when filter paper is present is mitigated. The instant disclosure solves this problem and more.

BRIEF SUMMARY

The quantization of DNA plays a central role in many applications including medical diagnostics and forensic DNA analysis. Often DNA used in these applications is derived from blood or buccal samples applied to filter paper. Quantification of the DNA then requires the extraction and removal of the DNA from its source and the filter paper using any one of a variety of methods. These methods include washing, Chelex® extraction, phenol/chloroform, silica membranes, silica-coated beads, ion exchange membranes and magnetic beads with an ionic surface. Problems with such methods include DNA sample loss and they are laborious.

A workflow which removes the necessity of extraction and removal would be advantageous. Depositing the filter paper into the qrtPCR without first applying these extraction and removal methods is a solution. But inclusion of filter paper during qrtPCR affects the baseline fluorescent level. Because of this, DNA quantification without extraction and removal is seldom attempted.

What was not been previously recognized, but is disclosed herein is that a source of the increased levels of background fluorescence is the presence of a Minor Groove Binder (MGB) in the qrtPCR assay. That is, in a comparison between direct quantification assays where an MGB is present to the same assay lacking an MGB, the assay lacking an MGB will have relatively lower background fluorescence.

Disclosed herein therefore is a method for directly quantifying nucleic acids without prior application of extraction techniques, the method encompassing depositing a solid support into a reaction vessel, performing a qrtPCR employing a probe while the solid support is within the reaction vessel and detecting the level of fluorescence emitted from the vessel, wherein a minor groove binder (MGB) is not present in the reaction mixture. In other embodiments a method for directly quantifying nucleic acids without prior application of extraction techniques is disclosed, the method encompassing depositing a solid support into a reaction vessel, performing a qrtPCR employing a probe without a MGB while the solid support is within the reaction vessel and detecting the level of fluorescence emitted from the vessel.

In some embodiments, the probe is a 5'-exonuclease probe lacking an MGB. In other embodiments, the method encompasses providing a 5'-exonuclease probe lacking an MGB.

In some embodiments, the probe of the method encompasses in a 5' to 3' order, a target binding region and a tail encompassing a linker and a template binding region, wherein the target binding region is complementary to an extension product of the probe and wherein an MGB is not present in the reaction vessel. In other embodiments, the method encompasses a probe wherein the probe encompasses in a 5' to 3' order, a target binding region and a tail encompassing a linker and a template binding region, wherein the target binding region is complementary to an extension product of the probe and wherein the probe lacks an MGB.

In other embodiments, the method encompasses providing a probe wherein the probe encompasses in a 5' to 3' order, a target binding region and a tail encompassing a linker and a template binding region, wherein the target binding region is complementary to an extension product of the probe and wherein the probe lacks an MGB.

In some embodiments the solid support is filter paper. In other embodiments, the method encompasses providing the solid support.

Also disclosed herein is a kit, the kit encompassing a DNA polymerase, a 5'-exonuclease probe with a 5' signaling moiety and a 3' quenching moiety but lacking a MGB, wherein the probe does not form a stable stem-loop structure and a primer pair wherein the primer pair hybridizes and flanks a target sequence found on more than one chromosome.

In some embodiments, the kit encompasses a 5'-exonuclease with a 5' signaling moiety and a 3' quenching moiety but lacking a MGB. In other embodiments, the kit encompasses a 5'-exonuclease probe with a 5' quenching moiety and a 3' signaling moiety lacking an MGB.

DESCRIPTION OF THE DRAWINGS

FIG. 1A—No punch, FIG. 1B—0.5 mm diameter, FIG. 1C—1.0 mm diameter, FIG. 1D—2.0 mm diameter.

FIG. 2A—No punch, FIG. 2B—0.5 mm diameter, FIG. 2C—1.0 mm diameter, FIG. 2D—2.0 mm diameter.

FIG. 3A—Quantifier® Duo reaction buffer. FIG. 3B—Quantifier® Trio reaction buffer. Probes conjugated with MGBs showed increased background fluorescent in the presence of 0.5 mm diameter paper punch relative to probes labeled with the same fluorescent dye but without a conjugated MGB.

FIG. 4A—Probe conjugated with MGB, Y-chromosome target; FIG. 4B—Probe conjugated with MGB, autosomal target; FIG. 4C—Probe without a conjugated MGB, Y-chromosome target; FIG. 4D—Probe without a conjugated MGB, autosomal target.

FIG. 5A—Scorpions® probe without a conjugated MGB, Y-chromosome target; FIG. 5B—Scorpions® probe without a conjugated MGB, autosomal target.

DETAILED DESCRIPTION

Figure 1A:
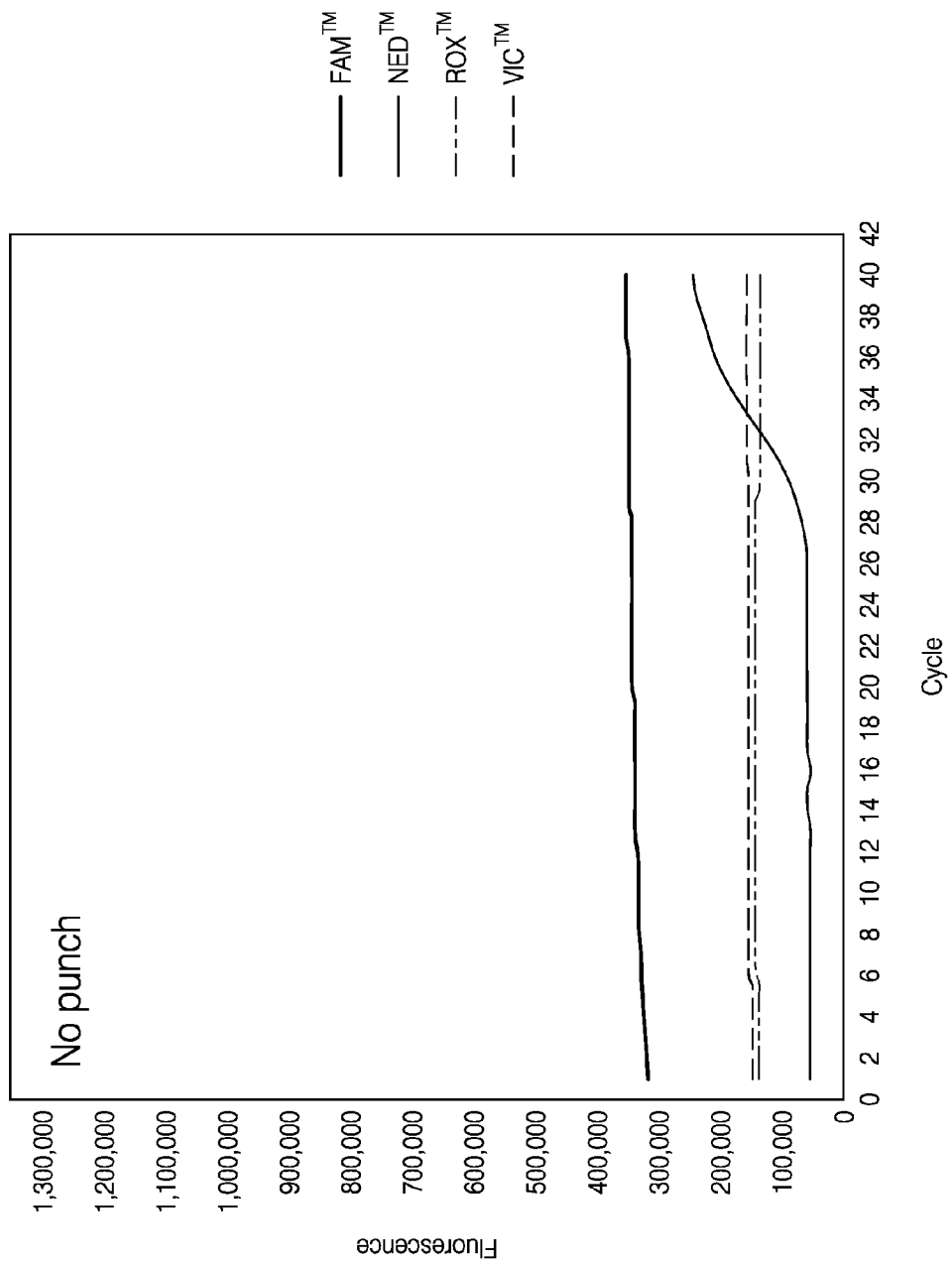
FIGS. 1A, 1B, 1C and 1D show the effect of a paper punch on fluorescent detection using a Quantifiler® Duo quantitative real-time PCR assay. When paper is present in the reaction vessel an increase in background fluorescence is witnessed with all the tested dyes except the ROX™ dye. The increase in background fluorescence appears to correlate with the size of the paper punch.
Figure 1B:
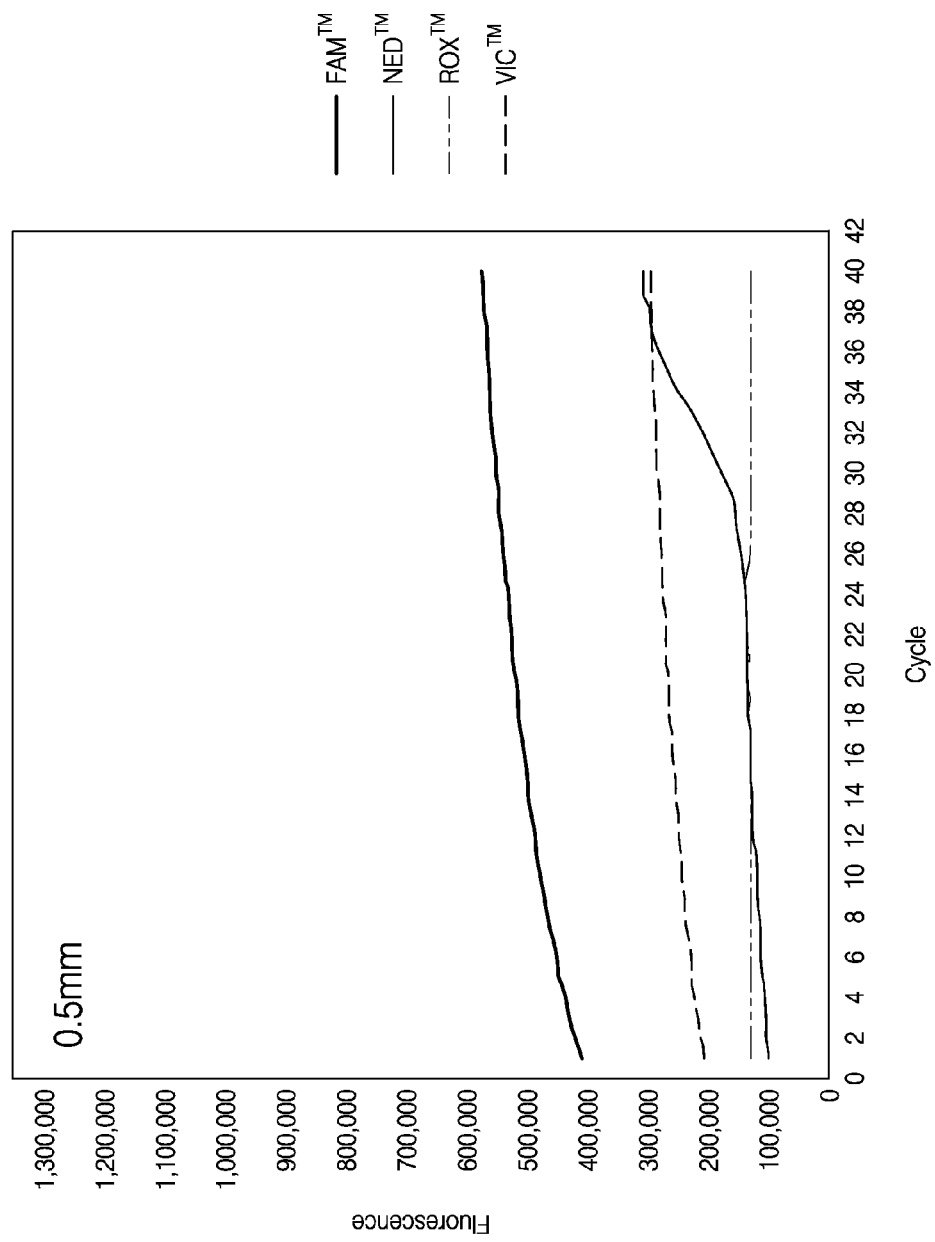
Figure 1C:
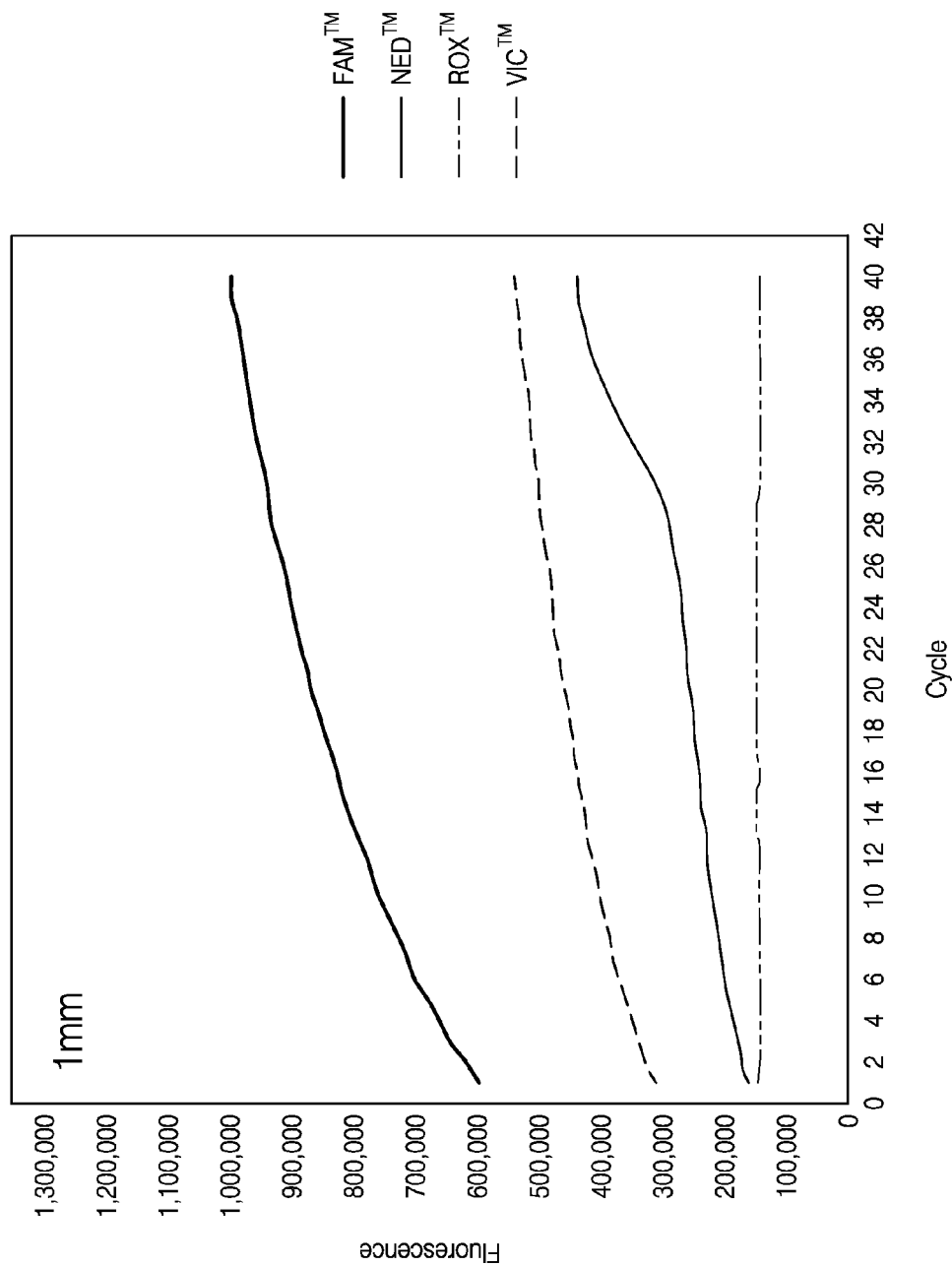
Figure 1D:
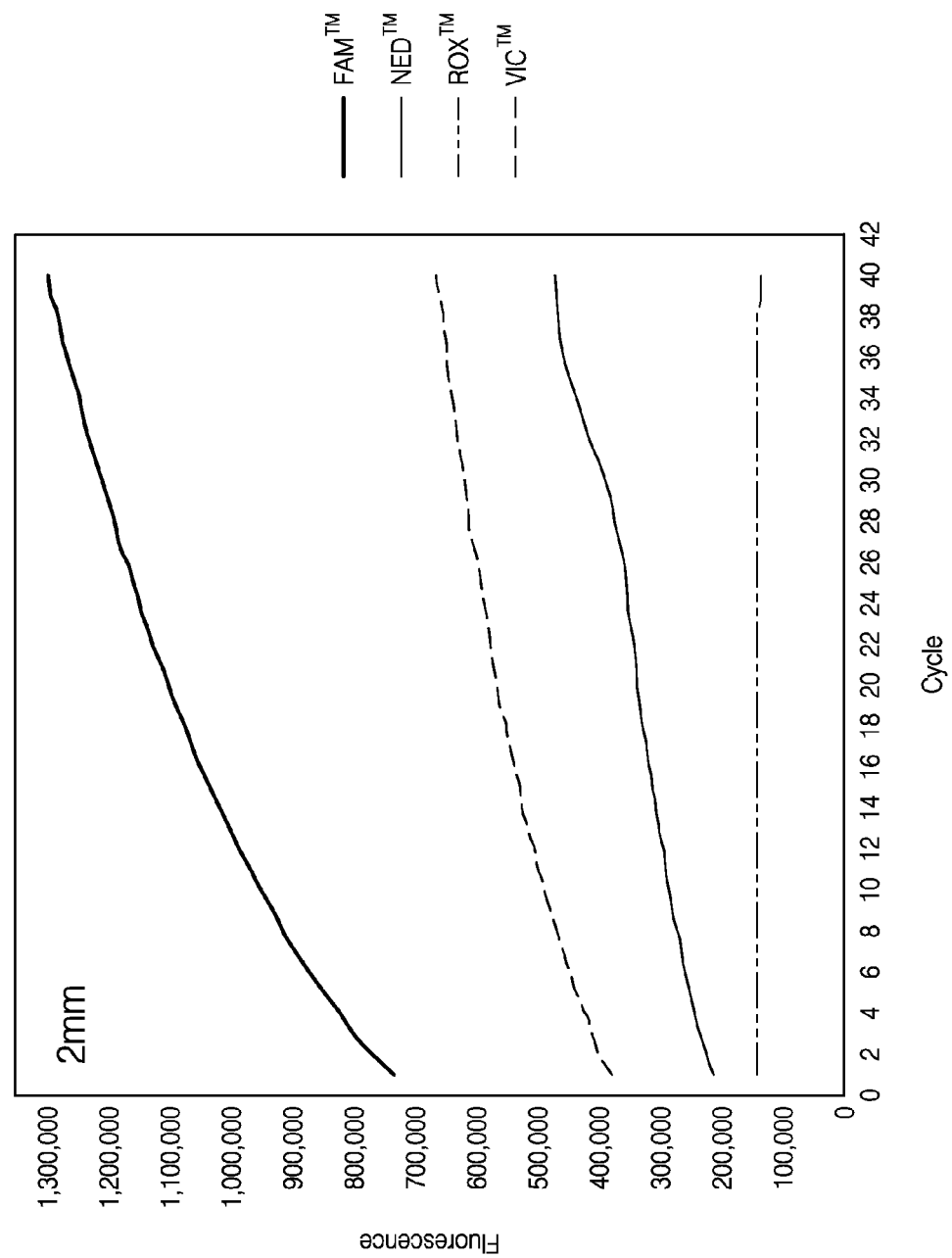
Figure 2A:
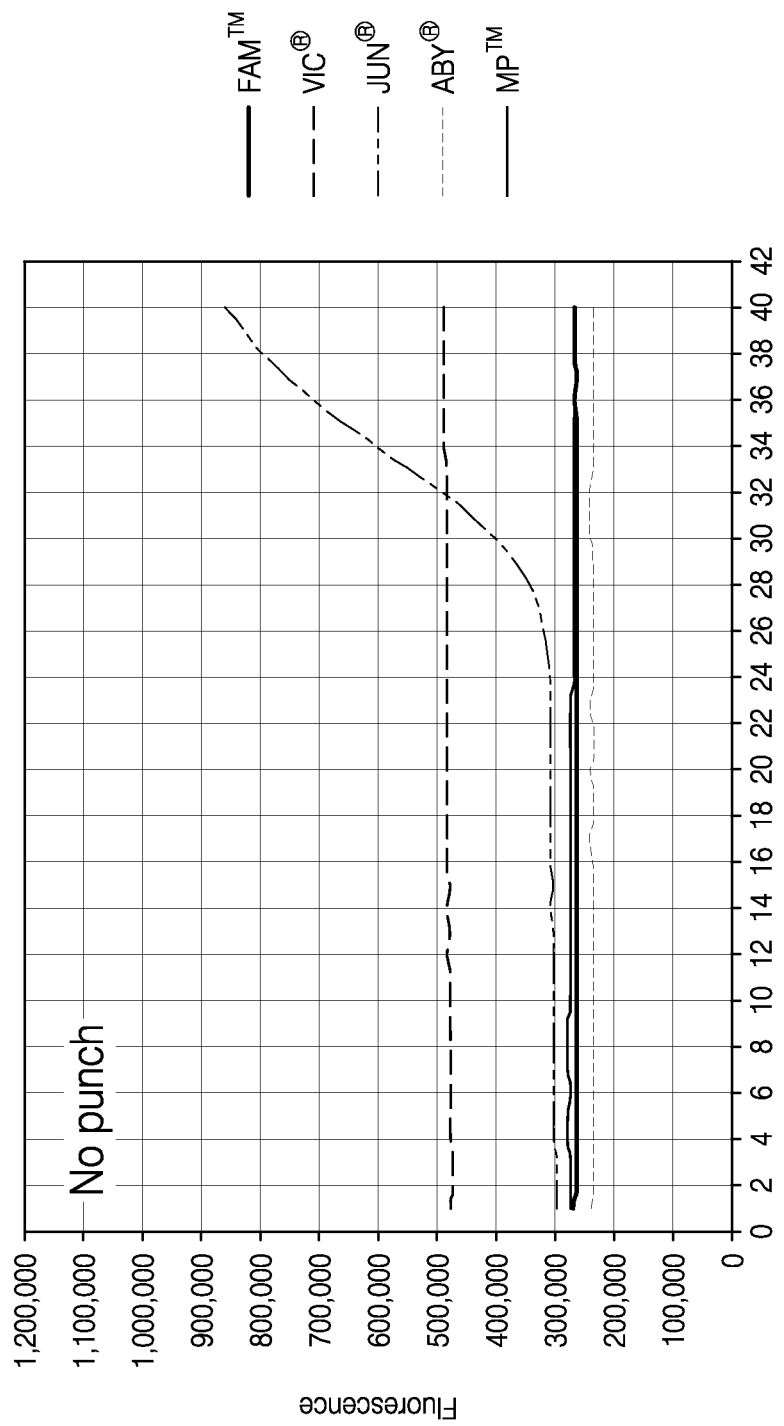
FIGS. 2A, 2B, 2C, and 2D show the effect of a paper punch on fluorescent detection using a Quantifier® Trio quantitative real-time PCR assay. An increase in background fluorescence is witnessed in the FAM™ and VIC® dyes but not the JUN®, ABY® and MUSTANG PURPLE™ dyes when paper is present in the reaction and apparently correlates with the size.
Figure 2B:
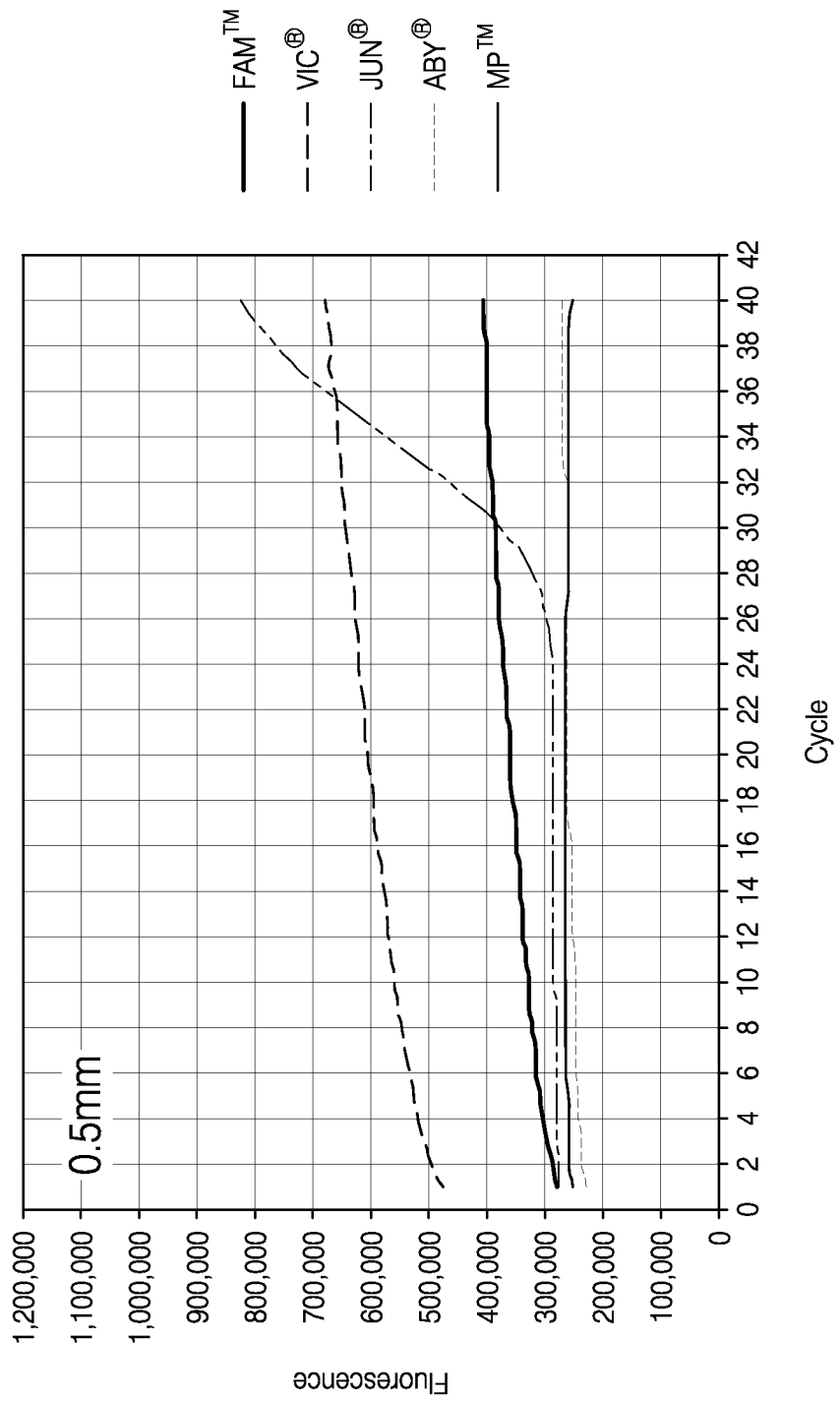
Figure 2C:
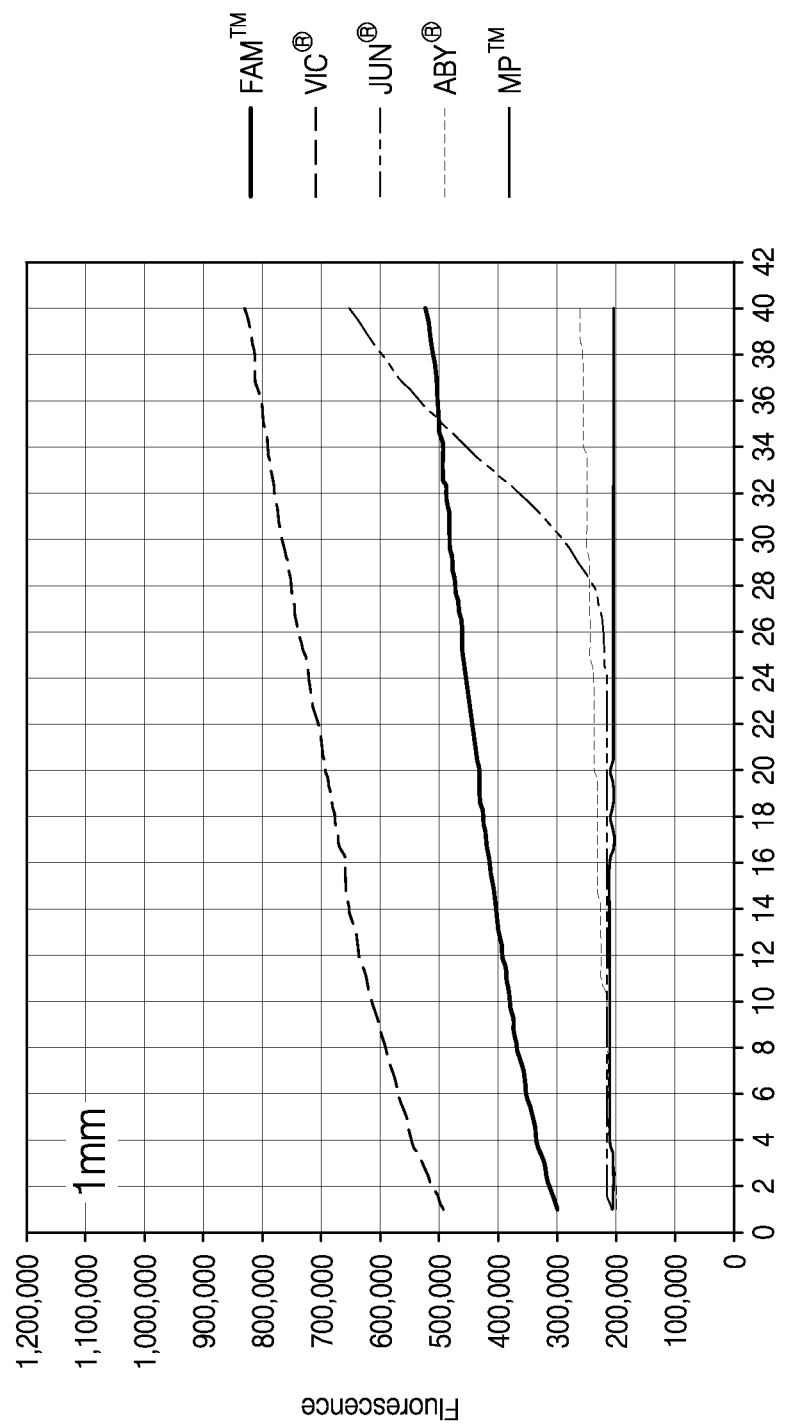
Figure 2D:
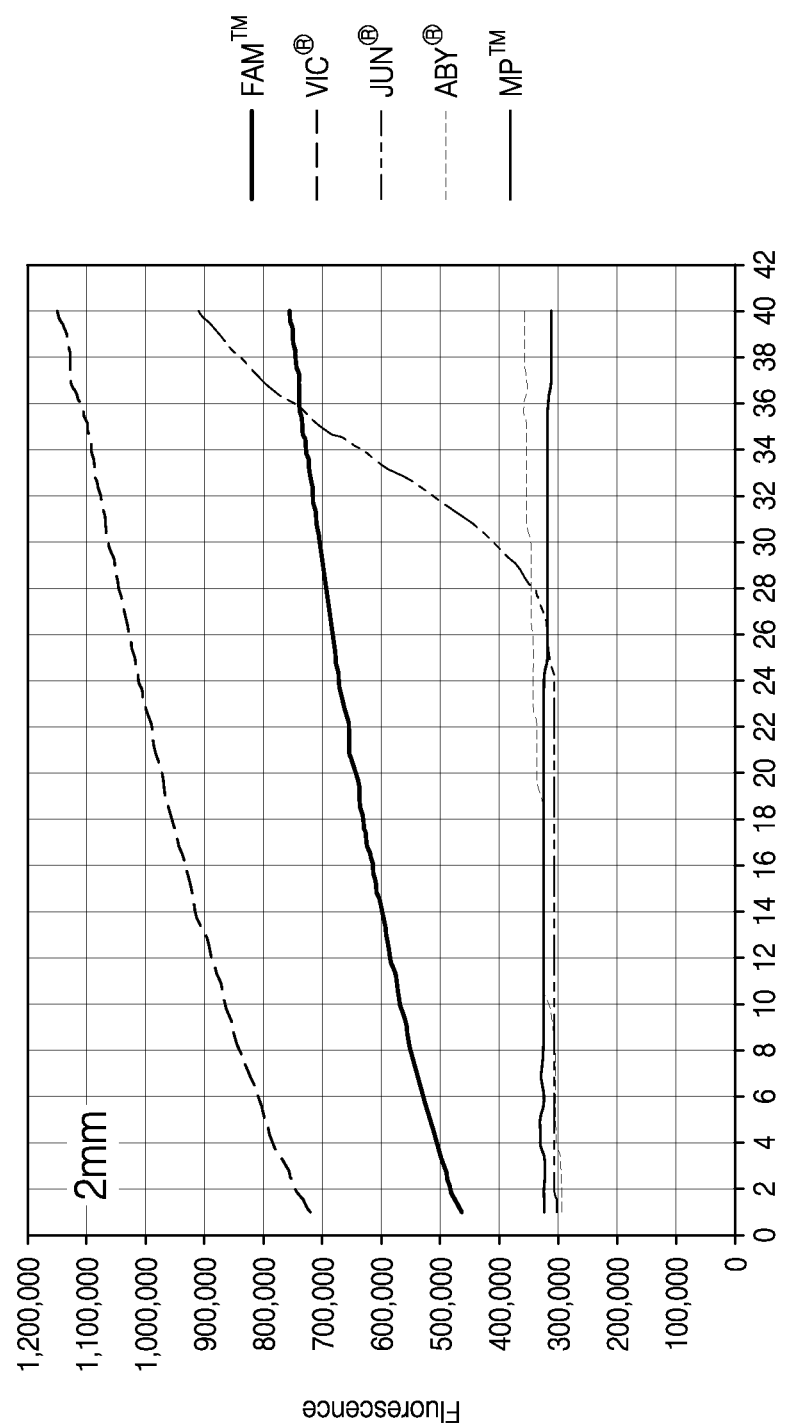

Quantitative Real Time Polymerase Chain Reaction (qrt-PCR), also referred to as Quantitative Polymerase Chain Reaction (qPCR), is a method based on PCR which allows for the quantification of a target nucleic acid molecule during the thermal cycling process. The standard method of qrtPCR involves suspending a nucleic acid in a liquid, combining this DNA containing liquid with a reaction mixture and preforming the qrtPCR assay. In a recently describe alternative to this method, a solid support with embedded nucleic acid is combined with a reaction mixture and the qrtPCR assay is conducted while the solid support is present. This alternative methodology has been called direct quantification.

"Direct quantification" refers generally to a method wherein a qrtPCR is conducted while a solid support, such as filter paper, is present in the reaction vessel. The theme driving direct quantification is a minimization in the number or complexity of manipulations necessary to conduct a qrtPCR assay. Thus, direct quantification includes instances wherein the solid support is not treated before depositing in the reaction vessel. Treatments include the application of extraction methods, buffers or washing, for example washing with solvent such as water, prior to depositing the solid support in a reaction vessel for qrtPCR.

Extraction methods include Chelex® extraction, the application of phenol/chloroform, the application of silica-coated beads, the application of ion exchange membranes and the application of magnetic beads with an ionic surface.

An example of a workflow encompassing direct quantification would be the application of a specimen, for instance blood or buccal sample, to a filter paper, drying the specimen on the filter paper, excising a portion of the filter paper, for example a disk, and depositing the disk in a reaction vessel for qrtPCR without contacting the dried specimen to a liquid until the qrtPCR assay.

Several groups have reported results from direct quantification assays. Each of these groups observed increased background fluorescence with filter paper. Taylor reported, for instance, a direct quantification assay for malarial parasites from blood spotted on 3 MM paper. Taylor detected fluorescence from the general DNA binding dye SYBR® Green to quantify the parasites. Taylor teaches that the filter paper was responsible for higher background.

Liu reported a direct quantification assay for total human DNA and human male DNA in a sample. Liu used a TaqMan® probe and noted increased background fluorescence associated with the presence of paper in the assay.

Nozawa used direct quantification for quantifying cytomegalovirus present in dried urine. Nozawa teaches that nonspecific signals from the disks interfere with the qrtPCR assay. Nozawa suggests that this is associated with the type of fluorescent detection system employed; photomultiplier tube or charge-coupled device camera.

Thus, in each reported application of direct quantification it was noted that increased background fluorescence was the result of, or associated with, the presence of paper. Several explanations for the increased background fluorescence associated with the presence of paper include the fluorescent characteristics of the paper, the paper source and changes in the orientation of the paper in the reaction well.

A driving assumption for further research was that the physical or chemical properties of the paper were responsible for the observed increase in background fluorescence. Contrary to expectations, the paper is not a major source for increasing background fluorescence in direct quantification assays.

The Quantifiler® Duo and the Quantifiler® Trio are two commercially available qrtPCR assays largely marketed to forensic scientists. The Quantifiler® Duo assay quantifies the amount of human DNA and human male DNA present in a sample. The Quantifiler® Trio assay also quantifies the amount of human DNA and human male DNA present in a sample. A difference between the two kits is that whereas the Quantifiler® Duo detects a single human autosomal target, the Quantifiler® Trio detects two different human autosomal targets. Because the Quantifiler® Trio detects one more target than the Quantifiler® Duo, the Quantifiler® Trio uses one more dye labeled probe.

Both assays use a probe labeled with a FAM™ dye and a probe labeled with a VIC® dye. The Quantifiler® Duo assay also uses the NED™ dye and the ROX™ dye, with the ROX™ dye representing a passive reference control. The Quantifiler® Trio assay differs from the Quantifiler® Duo assay in that the NED™ dye and the ROX™ dye are not present but the ABY® dye, JUN® dye and Mustang Purple™ dye are. Mustang Purple™ represents the passive reference control in the Quantifiler® Trio assay.

Both the Quantifiler® Duo and the Quantifiler® Trio assays were tested in direct quantification experiments. In both assays, the presence of paper resulted in increased background in the FAM™ dye and the VIC® dye fluorescence channels. In the Quantifiler® Duo assay there was an increase in the background fluorescence with the NED™ dye labeled probe. The increase in background correlated with larger paper disk size and cycle number (FIG. 1). Because the increased background correlated with the paper size, this argued strongly for the predominant belief that the paper was responsible for the increased background.

What these experiments revealed also was that the increased background apparently correlated with wavelength. TABLE 1 below shows the absorption and emission maxima of the dyes used in the Quantifiler® Duo and the Quantifiler® Trio assays. Increased background fluorescence was observed with FAM™, VIC® and NED™ but not the other dyes (FIGS. 1 and 2). These dyes all have an emission maximum below 586 nm. Those dyes with an emission maximum above 575 nm did not experience increased background; ABY®, ROX™, JUN® and MUSTANG PURPLE™. The data suggests therefore that the paper is causing increased background by emitting fluorescence in wavelengths below 586 nm.

TABLE 1

| DYE | ABSORPTION $\lambda_{max}$/nm | EMISSION $\lambda_{max}$/nm |
| --- | --- | --- |
| FAM ™ | 494 | 518 |
| VIC ® | 538 | 554 |
| NED ™ | 546 | 575 |
| ABY ® | 568 | 586 |
| ROX ™ | 575 | 602 |
| JUN ® | 606 | 618 |
| MUSTANG PURPLE ™ | 633 | 656 |

These assays were performed using an Applied Biosystems® 7500 real time PCR instrument. Interestingly, the filters of the Applied Biosystems® 7500 real time PCR instrument are configured such that fluorescent signals from the NED™ dye and the ABY® dye are detected together. If a fluorescent property of the paper was responsible for the background then the expectation would be that both the NED™ dye and the ABY® dye would have been affected similarly. But since the background fluorescence differs between the two, this argued that something other than the general spectral properties of paper was responsible. This left any number of possible variables to explore.

Minor Groove Binders

A distinction between the probe labeled with the NED™ dye and the probe labeled with ABY® dye was the presence or absence of a minor groove binder (MGB). "Minor Groove Binder" (MGB) refers to a moiety typically having a molecular weight of approximately 150 to approximately 2000 Daltons. The moiety binds in a non-intercalating manner into the minor groove of double stranded (or higher order aggregation) DNA, RNA or hybrids thereof, preferably, with an association constant greater than approximately $10^3$ $M^{-1}$.

This type of binding can be detected by established spectrophotometric methods, such as ultraviolet (u.v.) and nuclear magnetic resonance (nmr) spectroscopy and also by gel electrophoresis. Shifts in u.v. spectra upon binding of a minor groove binder molecule, and nmr spectroscopy utilizing the "Nuclear Overhauser" (NOSEY) effect are particularly well known and useful techniques for this purpose. Gel electrophoresis detects binding of a minor groove binder to double stranded DNA or fragment thereof, because upon such binding the mobility of the double stranded DNA changes.

Oligonucleotides conjugated with MGBs form unusually stable hybrids with complementary DNA. MGBs increase the melting temperature of probes with their target sequence, allowing for the design of shorter probes. The minor groove binder is typically attached to the oligomer through a linker comprising a chain about 20, about 15 atoms, about 10 or about 5 atoms.

Because probes utilizing MGBs are relatively shorter they have reduced background fluorescence due to decreased distance between a reporter and a quencher. Because of these properties they are widely used in qrtPCR.

Minor groove binding compounds have widely varying chemical structures; however, exemplary minor groove binders have a crescent shape three dimensional structure. Examples of MGBs include certain naturally occurring compounds such as netropsin, distamycin and lexitropsin, mithramycin, chromomycin $A_3$, olivomycin, anthramycin, sibiromycin, as well as further related antibiotics and synthetic derivatives. Certain bisquarternary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI) as well as a number of oligopeptides, such as the tripeptide 1,2-dihydro-(3H)-pyrrolo[3,2-e]indole-7-carboxlate (CDPI$_3$), consisting of naturally occurring or synthetic amino acids are minor groove binder compounds. Exemplary minor groove binders are described in U.S. Pat. No. 6,084,102.

Intercalating moieties or agents are readily distinguished from minor groove binders on the basis that the intercalating agents are flat aromatic (preferably polycyclic) molecules versus the "crescent shape" or analogous geometry of the minor groove binders. An experimental distinction can also be made by nmr spectroscopy utilizing the NOSEY effect.

Figure 3A:
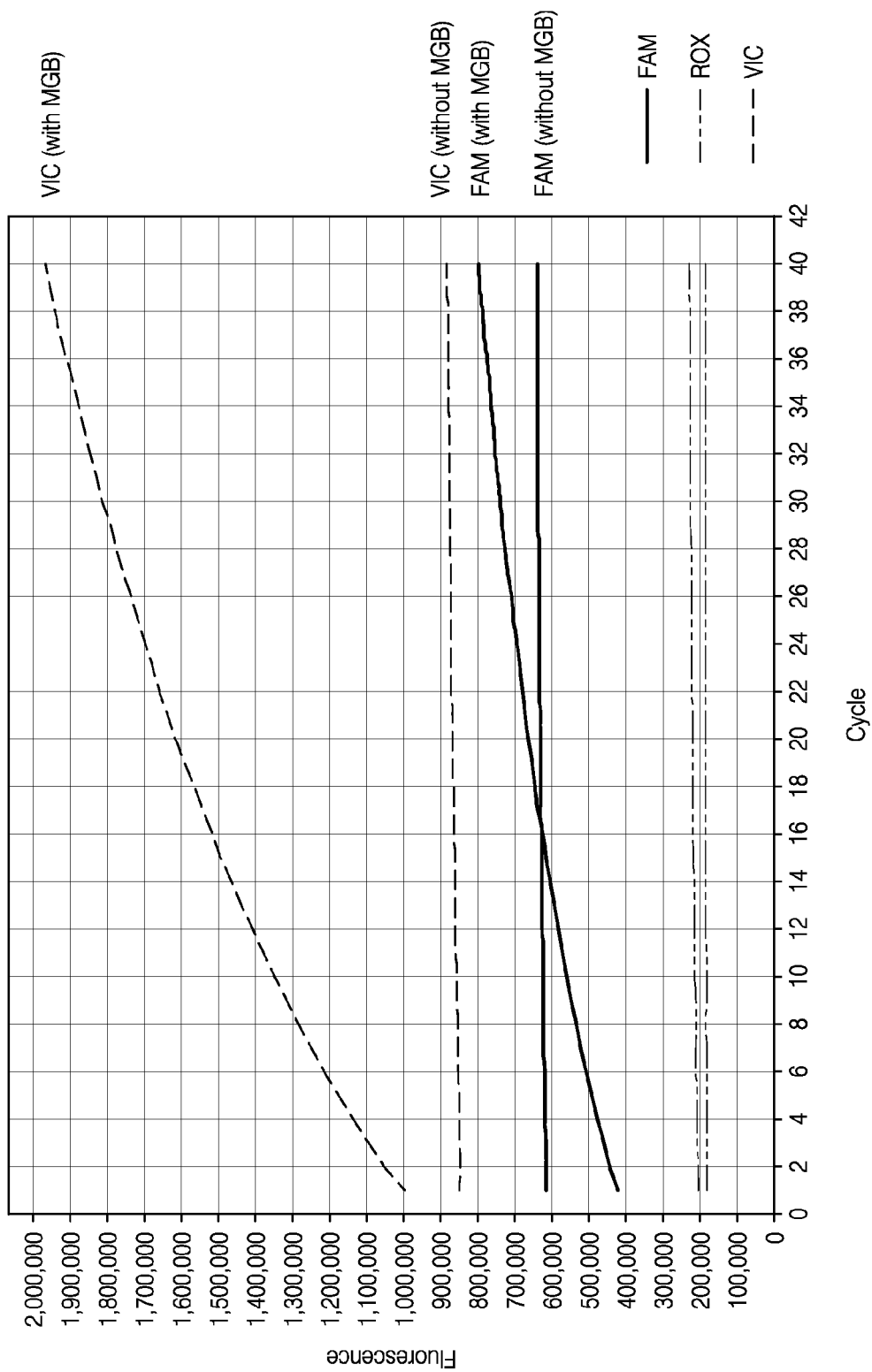
FIGS. 3A and 3B show the effect of paper punch on background fluorescence with probes with or without conjugation to a minor groove binder (MGB).
Figure 3B:
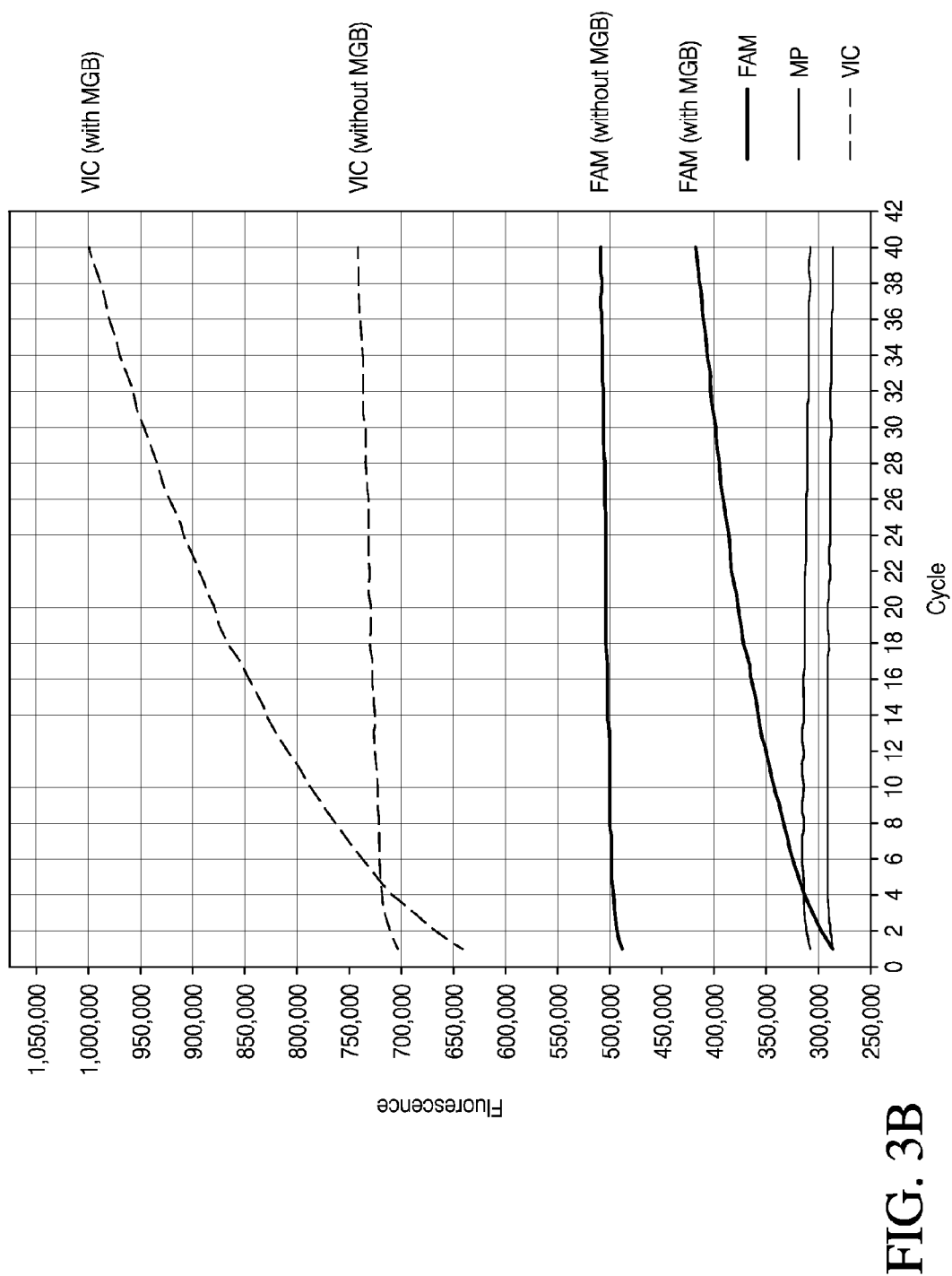

MGBs are not recognized as being responsible for increasing background fluorescence. Yet, when probes with the same fluorescent label, with and without MGBs were tested in the presence of paper, there was drastic differences in the levels of background fluorescence (FIG. 3). Those reactions with MGB had relatively higher background compared to those lacking MGB.

Accordingly, in some embodiments a method is disclosed, the method encompassing combining a fluorescently labeled probe and a solid substrate in a reaction vessel, preforming a quantitative real-time polymerase chain reaction and detecting a level of fluorescence emanating from the reaction vessel during a thermal cycle, wherein a minor groove binder (MGB) is not present in the reaction vessel. In some embodiments, the solid support is untreated.

In some embodiments, a method is disclosed encompassing combining a fluorescently labeled probe and a solid substrate in a reaction vessel, preforming a quantitative real-time polymerase chain reaction and detecting a level of fluorescence emanating from the reaction vessel during a thermal cycle, wherein the probe is not conjugated to an MGB.

Probes

"Probe" refers to nucleic acid oligonucleotides prepared using a solid support. In various embodiments, the probes produce a detectable response upon interaction with a target. The probes include at least one detectable moiety, or a pair of moieties that form an energy transfer pair detectable upon some change of state of the probe in response to its interaction with a target.

Oligonucleotides conjugated with MGBs find particular use as probes in qrtPCR assays. Examples of probe based technologies employed in qrtPCR assays include 5'-exonuclease, molecular beacons, hybridization probes and Scorpions® probe.

5'-exonuclease probes, an example of which is a TaqMan™ probe, are oligonucleotides that contain fluorophore and quencher moieties preferably located on 5' and 3' termini. Assays employing 5'-exonuclease probes rely on the 5'-exonuclease activity of Taq polymerase to measure the amount of target sequence in a sample.

During qrtPCR, the complementary strands of a target DNA sequence are melted apart. When complementary strands of the target DNA are separate a 5'-exonuclease probe, the reverse complement of one of the strands, can hybridize to the target. Polymerase mediated extension of a primer occurs. When the extending strand reaches the 5'-exonuclease probe, the probe is degraded. This separates the flourophore from the quencher, resulting in a fluorescent signal. The fluorescent signal is proportional to the amount of target present.

"Complementary" refers to sequence complementarity between two different nucleic acid strands or between two regions of the same nucleic acid strand. A first region of a nucleic acid is complementary to a second region of the same or a different nucleic acid if, when the two regions are arranged in an anti-parallel fashion, at least one nucleotide residue of the first region is capable of base pairing (that is, hydrogen bonding) with a residue of the second region, thus forming a hydrogen-bonded duplex.

"Substantially complementary" refers to two nucleic acid strands (for example, a strand of a target nucleic acid and a complementary single-stranded oligonucleotide probe) that are capable of base pairing with one another to form a stable hydrogen-bonded duplex under stringent hybridization conditions. In general, "substantially complementary" refers to two nucleic acids having at least 70%, for example, about 75%, 80%, 85%, 90%, 95%, 97%, 98%, 99% or 100% complementarity.

In some embodiments a method is disclosed, the method encompassing combining a fluorescently labeled probe and a solid substrate in a reaction vessel, preforming a quantitative real-time polymerase chain reaction and detecting a level of fluorescence emanating from the reaction vessel during a thermal cycle while the solid support is present in the reaction vessel, wherein a fluorophore is present at the 5' terminus of the probe and a quencher is present at the 3' terminus of the probe and wherein a minor groove binder (MGB) is not present in the reaction vessel. In some embodiments, a quencher is present at the 5' terminus of the probe and a fluorophore is present at the 3' terminus of the probe. In other embodiments, the solid support is untreated.

In other embodiments a method is disclosed, the method encompassing combining a fluorescently labeled probe and a solid support in a reaction vessel, preforming a quantitative real-time polymerase chain reaction and detecting a level of fluorescence emanating from the reaction vessel during a thermal cycle while the solid support is present in the reaction vessel, wherein a fluorophore is present at the 5' terminus of the probe and a quencher is present at the 3' terminus of the probe and wherein a minor groove binder (MGB) is not conjugate to the probe. In some embodiments, the MGB is not conjugated to the 3' terminus of the probe.

In other embodiments, the MGB is not conjugated to the 5' terminus of the probe. In other embodiments, the solid support is untreated.

In other embodiments, a method is disclosed encompassing providing a fluorescently labeled probe, combining the fluorescently labeled probe and a solid support in a reaction vessel, preforming a quantitative real-time polymerase chain reaction and detecting a level of fluorescence emanating from the reaction vessel during a thermal cycle while the solid support is present in the reaction vessel, wherein a fluorophore is present at the 5' terminus of the probe and a quencher is present at the 3' terminus of the probe and wherein a minor groove binder (MGB) is not present in the reaction vessel. In other embodiments, the solid support is untreated.

In other embodiments a method is disclosed, the method encompassing providing a fluorescently labeled probe, combining the fluorescently labeled probe and a solid substrate in a reaction vessel, preforming a quantitative real-time polymerase chain reaction and detecting a level of fluorescence emanating from the reaction vessel during a thermal cycle while the solid support is present in the reaction vessel, wherein a fluorophore is present at the 5' terminus of the probe and a quencher is present at the 3' terminus of the probe and wherein a minor groove binder (MGB) is not conjugate to the probe. In some embodiments, the MGB is not conjugated to the 3' terminus of the probe. In other embodiments, the MGB is not conjugated to the 5' terminus of the probe. In other embodiments, the solid support is untreated.

"Fluorophore" refers to a moiety that is inherently fluorescent or demonstrates a change in fluorescence upon binding to a biological compound or metal ion, or when metabolized by an enzyme. Numerous fluorophores are known, examples of which include coumarins, acridines, furans, dansyls, cyanines, pyrenes, naphthalenes, benzofurans, quinolines, quinazolinones, indoles, benzazoles, borapolyazaindacenes, oxazines and xanthenes, with the latter including fluoresceins, rhodamines, rosamines and rhodols.

A number of fluorescent dyes can be detected in a qrtPCR assay and can include, without limitation, the following: 5- or 6-carboxyfluorescein (FAM™), VIC™, NED™, fluorescein, fluorescein isothiocyanate (FITC), IRD-700/800, cyanine dyes, such as CY3™, CY5™, CY3.5™, CY5.5™, Cy7™, xanthen, 6-carboxy-2',4',7',4,7-hexachlorofluorescein (HEX™), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX™), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as Texas Red®, California Red®, Yakima Yellow, Alexa Fluor® 350, Alexa Fluor® 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rho1 1, Atto Rho12, Atto Rho101, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3', 6'-dipivaloylfluorescein-6-carboxamido)-hexyl-1-0-(2-cyanoethyl)-(N,N-diisopropyl)-phosphoramidite (SIMA), CAL Fluor® Gold 540, CAL Fluor® Orange 560, CAL Fluor Red 635, Quasar® 570, Quasar® 670, LIZ, Sunnyvale Red, LC Red® 610, LC Red® 640, LC Red®670 and LC Red®705.

"Quencher" refers to any fluorescent-modifying moiety that can attenuate at least partly the light emitted by a fluorophore. This attenuation is referred to as "quenching." The excitation of a fluorophore in the presence of the quenching group leads to an emission signal that is less intense than expected, or even completely absent. Quenching typically occurs through energy transfer between the excited fluorophore and the quenching group.

Very little fluorescence is emitted from intact 5'-exonuclease probe due to efficient intra-molecular quenching. However, during PCR amplification, the probe specifically hybridizes to its target sequence and the 5'-3'-exonuclease activity of Taq polymerase cleaves the probe between fluorophore and quencher moieties. "Hybridize" refers to two nucleic acid strands associated with each other which may or may not be fully base-paired.

Molecular beacons are single-stranded oligonucleotide probes that are non-fluorescent in isolation, but become fluorescent upon hybridization to target sequences. Non-hybridized molecular beacons form stem-loop structures, possessing a fluorophore covalently linked to one end of the molecule and a quencher linked to the other, such that the hairpin of the beacon places the fluorophore moiety in close proximity with the quencher. When molecular beacons hybridize to target sequences, fluorophore and quencher moieties become spatially separated, such that the fluorophore is no longer quenched and the molecular beacon fluoresces. The secondary structure of the molecular beacon conveys high specificity to the hybridization probe.

Accordingly, in some embodiments a method is disclosed, the method encompassing combining a fluorescently labeled probe and a solid substrate in a reaction vessel, preforming a quantitative real-time polymerase chain reaction and detecting a level of fluorescence emanating from the reaction vessel during a thermal cycle while the solid support is present in the reaction vessel, wherein the probe possesses a self-complementary sequence and wherein a minor groove binder (MGB) is not present in the reaction vessel. In some embodiments, the self-complementary sequence forms a hairpin. In other embodiments, the solid support is untreated.

In some embodiments, the method encompasses combining a fluorescently labeled probe and a solid substrate in a reaction vessel, preforming a quantitative real-time polymerase chain reaction and detecting a level of fluorescence emanating from the reaction vessel during a thermal cycle while the solid support is present in the reaction vessel, wherein the probe possesses a self-complementary sequence and wherein a minor groove binder (MGB) is not conjugated to the probe. In some embodiments, the self-complementary sequence of the probe forms a hairpin and an MGB is not conjugated to the probe. In other embodiments, the solid support is untreated.

In some embodiments, the method encompasses providing a fluorescently labeled probe, wherein the probe possesses a self-complementary sequence and wherein an MGB is not conjugated to the probe. In some embodiments, method encompasses providing a probe possessing a self-complementary sequence wherein the self-complementary sequence of the probe forms a hairpin and an MGB is not conjugated to the probe.

Hybridization probes are oligonucleotides that are singly labeled with a fluorophore moiety. Two such oligonucleotides are required for each hybridization probe assay, one labeled with a donor fluorophore and the other with an acceptor fluorophore. Fluorescein is commonly employed as the donor and Cy5™, LC Red® 640 and LC Red®705 are commonly used as acceptors. Excitation of the donor fluorophore produces an emission spectrum that overlaps with the absorption spectrum of the acceptor fluorophore. Hybridization probe pairs are designed to recognize adjacent nucleotide sequences within target molecules. In isolation, the acceptor oligonucleotide is not excited and does not generate a fluorescent signal. However, during hybridization to polynucleotide target sequences, the donor and acceptor probes are brought into close proximity, allowing fluorescence resonance energy transfer from the donor to the acceptor. Fluorescent signal from the acceptor fluorophore is only emitted when both probes are hybridized to the target molecule. When incorporated into PCR reactions, fluorescence from the acceptor probe is monitored once per cycle of amplification, to facilitate real-time measurement of product accumulation, where the amount of fluorescence emitted by the acceptor is proportional to the quantity of target synthesized.

In some embodiments, the method encompasses combining a probe labeled with a donor fluorophore, a probe labeled with an acceptor fluorophore and a solid substrate in a reaction vessel, preforming a quantitative real-time polymerase chain reaction and detecting a level of fluorescence emanating from the reaction vessel during a thermal cycle while the solid support is present in the reaction vessel and wherein an MGB is not present in the reaction vessel. In other embodiments, the solid support is untreated.

In other embodiments, the method encompasses combining a probe labeled with a donor fluorophore, a probe labeled with an acceptor fluorophore and a solid substrate in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not conjugated to either probe. In some embodiments, an MGB is conjugated to the probe labeled with a donor fluorophore. In other embodiments, an MGB is conjugated to the probe labeled with an acceptor fluorophore. In other embodiments, the solid support is untreated.

In some embodiments, the method encompasses providing a probe labeled with a donor fluorophore, combining the probe labeled with the donor fluorophore, a probe labeled with an acceptor fluorophore and a solid substrate in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not conjugated to either probe.

In other embodiments, the method encompasses providing a probe labeled with an acceptor fluorophore, combining a probe labeled with a donor fluorophore, the probe labeled with an acceptor fluorophore and a solid substrate in a reaction vessel while the solid support is present in the reaction vessel, preforming a quantitative real-time polymerase chain reaction and detecting a level of fluorescence emanating from the reaction vessel during a thermal cycle, wherein a minor groove binder (MGB) is not conjugated to either probe. In some embodiments, the method encompasses providing a probe labeled with an acceptor fluorophore conjugated with an MGB. In other embodiments, the method encompasses providing a probe labeled with a donor fluorophore conjugated with an MGB.

5'-exonuclease, molecular beacon and hybridization probe assays are bimolecular systems that have the probe and target sequences located on separate DNA strands. Scorpions® probes operate through single molecular binding events, where the probe and amplified target sequence are located on the same DNA strand. Single molecular binding events are kinetically favored over bimolecular hybridization. Scorpions® probes encompass a primer with an attached probe tail sequence, where the probe sequence is contained within a stem-loop secondary structure similar to that of a molecular beacon. In the non-extended form, Scorpions® primers are non-fluorescent due to fluorophore and quencher moieties being in close proximity. During PCR, the primer component of the Scorpions® probe is extended at its 3' end producing the homologous target sequence required for probe hybridization. When the Scorpions® probe sequence hybridizes to amplified target the fluorophore and quencher moieties become spatially separated generating significant increases in fluorescent signal concurrent with target amplification.

Accordingly, in some embodiments a method is disclosed, the method encompassing combining a fluorescently labeled probe and a solid substrate in a reaction vessel and preforming a quantitative real-time polymerase chain reaction and detecting a level of fluorescence emanating from the reaction vessel during a thermal cycle while the solid support is present in the reaction vessel, wherein the probe comprises in a 5' to 3' order, a target binding region and a tail comprising a linker and a template binding region, wherein the target binding region is complementary to an extension product of the probe and wherein a minor groove binder is not present in the reaction vessel. In other embodiments, the solid support is untreated.

When using a Scorpions® probe the "template" is the underlining nucleic acid sought to be quantified in a qrtPCR.

In other embodiments, the method encompasses combining a fluorescently labeled probe and a solid substrate in a reaction vessel and preforming a quantitative real-time polymerase chain reaction and detecting a level of fluorescence emanating from the reaction vessel during a thermal cycle while the solid support is present in the reaction vessel, wherein the probe comprises in a 5' to 3' order, a target binding region and a tail comprising a linker and a template binding region, wherein the target binding region is complementary to an extension product of the probe and wherein the probe is not conjugated with a minor groove binder (MGB). In other embodiments, the solid support is untreated.

In some embodiments, the method encompasses providing a probe, wherein the probe comprises in a 5' to 3' order, a target binding region and a tail comprising a linker and a template binding region, wherein the target binding region is complementary to an extension product of the probe, combining a fluorescently labeled probe and a solid substrate in a reaction vessel and preforming a quantitative real-time polymerase chain reaction and detecting a level of fluorescence emanating from the reaction vessel during a thermal cycle while the solid support is present in the reaction vessel and wherein a minor groove binder is not present in the reaction vessel.

In some embodiments, the method encompasses providing a probe, wherein the probe comprises in a 5' to 3' order, a target binding region and a tail comprising a linker and a template binding region, wherein the target binding region is complementary to an extension product of the probe, combining a fluorescently labeled probe and a solid substrate in a reaction vessel and preforming a quantitative real-time polymerase chain reaction and detecting a level of fluorescence emanating from the reaction vessel during a thermal cycle while the solid support is present in the reaction vessel and wherein the probe is not conjugated with a minor groove binder.

Instruments

The fluorescent signal emitted from the vessel during the qrtPCR can be detected using a number of different types of detectors including Charge-coupled Device (CCD), photodiode and photomultiplier tube. A CCD converts the light that it captures into digital data. The quality of the image captured is determined by the resolution, usually expressed in terms of megapixels. CCDs are typically used to capture an image of a vessel or reaction plate, whose content is then interpreted by instrument software.

A photodiode is a type of photodetector that, when exposed to light, causes a current to flow. A photomultiplier tube multiplies the current that is produced by incident light.

Accordingly, in some embodiments a method is disclosed, the method encompassing combining a fluorescently labeled probe and a solid substrate in a reaction vessel, preforming a quantitative real-time polymerase chain reaction and detecting a level of fluorescence emanating from the reaction vessel during a thermal cycle while the solid support is present in the reaction vessel, wherein the fluorescence is detected with a charged-coupled device and wherein a minor groove binder (MGB) is not present in the reaction vessel. In other embodiments, the fluorescence is detected with a photodiode. In some embodiments, the fluorescence is detected with a photomultiplier. In some embodiments, one or more probes in the reaction vessel are not conjugated with a MGB.

In some embodiments, fluorescence is detected and the quantity of a target is thereby determined.

In some embodiments, the method encompasses providing the qrtPCR instrument.

Samples

In some embodiments a method is disclosed, the method encompassing providing a solid support contacted to a surface, combining a fluorescently labeled probe and the solid support in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel. In other embodiments, the method encompasses providing a solid support contacted to a surface, combining a fluorescently labeled probe and the solid support in a reaction vessel, preforming a quantitative real-time polymerase chain reaction and detecting a level of fluorescence emanating from the reaction vessel during a thermal cycle while the solid support is present in the reaction vessel, wherein the probe is not conjugated with a minor groove binder (MGB).

In some embodiments, the method encompasses combining a fluorescently labeled probe and the solid support in a reaction vessel, wherein a biological sample has been applied to the solid support, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel. In other embodiments, the method encompasses combining a fluorescently labeled probe and the solid support in a reaction vessel, wherein a biological sample has been applied to the solid support, preforming a quantitative real-time polymerase chain reaction and detecting a level of fluorescence emanating from the reaction vessel during a thermal cycle while the solid support is present in the reaction vessel, wherein the probe is not conjugated with a minor groove binder (MGB). In other embodiments, the solid support is untreated.

In some embodiments, the surface contacted is suspected of having a biological sample or a specimen. In some embodiments, the solid support is contacted to a surface during the course of a criminal investigation.

A "biological sample" refers to a collection made from an organism such as a eukaryote, prokaryote or virus. In some embodiments, the biological sample is not a malarial parasite.

In some embodiments, the method encompasses combining a fluorescently labeled probe and the solid support in a reaction vessel, wherein a specimen has been applied to the solid support, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel. In other embodiments, the method encompasses combining a fluorescently labeled probe and the solid support in a reaction vessel, wherein a specimen has been applied to the solid support, preforming a quantitative real-time polymerase chain reaction and detecting a level of fluorescence emanating from the reaction vessel during a thermal cycle while the solid support is present in the reaction vessel, wherein the probe is not conjugated with a minor groove binder (MGB). In other embodiments, the solid support is untreated.

A "specimen" refers to whole blood, plasma, serum, saliva, buccal sample, sweat, vaginal secretions, semen, tissues, urine, cerebrospinal fluid and touch nucleic acid. "Touch nucleic acid" or "transfer nucleic acid" refers to nucleic acid that may be left on a surface after being contacted by an organism. For example, a fingerprint can contain nucleic acid and represents a touch nucleic acid. In some embodiments, the specimen is no urine. In some embodiments, the specimen is not from a child less than a month old.

In some embodiments, the method encompasses combining a fluorescently labeled probe, a primer or a primer pair and a solid support in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel. In other embodiments, a method is disclosed encompassing combining a fluorescently labeled probe, a primer or a primer pair and a solid support in a reaction vessel, preforming a quantitative real-time polymerase chain reaction and detecting a level of fluorescence emanating from the reaction vessel during a thermal cycle while the solid support is present in the reaction vessel, wherein the probe is not conjugated with a minor groove binder (MGB). In other embodiments, the solid support is untreated.

In some embodiments, the method encompasses providing a primer or a primer pair, combining a fluorescently labeled probe, the primer or the primer pair and a solid support in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel. In other embodiments, the method encompasses providing a primer or a primer pair, combining a fluorescently labeled probe, the primer or the primer pair and a solid support in a reaction vessel, preforming a quantitative real-time polymerase chain reaction and detecting a level of fluorescence emanating from the reaction vessel during a thermal cycle while the solid support is present in the reaction vessel, wherein the probe is not conjugated with a minor groove binder (MGB). In other embodiments, the solid support is untreated.

"Primer(s)" refer to isolated oligonucleotides that can anneal to a complementary nucleic acid strand and can be extended, for example by a polymerase. A primer pair refers to two primers that anneal to opposite strands of a DNA target. Primers flank a target.

"Target" refers to a nucleic acid sequence to be detected. Copies of the target sequence which are generated during the amplification reaction are referred to as amplification products, amplimers, or amplicons. A target nucleic acid may be composed of segments of a chromosome, a complete gene with or without intergenic sequence, segments or portions of a gene, with or without intergenic sequence. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. A target nucleic acid may be DNA or RNA from a eukaryotic cell or a nucleic acid copied or amplified therefrom but not a prokaryotic cell or virus. A target nucleic acid may be DNA or RNA from a prokaryotic cell or a nucleic acid copied or amplified therefrom but not a eukaryotic cell or virus. A target nucleic acid may be DNA or RNA from a virus but not a eukaryotic cell or prokaryotic cell.

In some embodiments, the target is a multicopy locus. A multicopy locus is not a repetitive element and has copies on at least two different chromosomes, for example chr. 1 and chr. 2 and chr. X and chr. Y. Two different chromosomes do not refer to one chromosome inherited from the mother and the other from the father. In some embodiments, the multicopy locus is one with 5-50 copies in the genome. In other embodiments, the multicopy locus is one with 10-40 copies in the genome. In some embodiments, the multicopy locus is one with 10-25 copies in the genome. In other embodiments, the multicopy locus is one with 13-20 copies in the genome. In some embodiments, the multicopy locus is one with 14-19 copies in the genome.

Accordingly, in some embodiments a method is disclosed, the method encompassing combining a fluorescently labeled probe and a solid support in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not present in the reaction vessel and a target is a multicopy locus. In other embodiments, a method is disclosed, the method encompassing combining a fluorescently labeled probe and a solid support in a reaction vessel, preforming a quantitative real-time polymerase chain reaction and detecting a level of fluorescence emanating from the reaction vessel during a thermal cycle while the solid support is present in the reaction vessel, wherein a minor groove binder (MGB) is not conjugated to the probe and a target is a multicopy locus. In other embodiments, the solid support is untreated.

In some embodiments, the disclosed method encompasses providing a fluorescently labeled probe, wherein the probe detects a multicopy locus. In other embodiments, the disclosed method encompasses providing a primer or a primer pair wherein the primer or the primer pair flanks a multicopy locus.

"Multiplex PCR" refers to the simultaneous amplification of more than one target polynucleotide in a vessel. In some embodiments, at least 2 targets are amplified simultaneously. In some embodiments, at least 3 targets are amplified simultaneously. In other embodiments, at least 4 targets are amplified simultaneously. In still other embodiments, at least 5 targets are amplified simultaneously. In other embodiments, at least 6 targets are amplified simultaneously. In some embodiments, 7 or more targets are amplified simultaneously.

Solid Support

"Paper" refers to sheet-like masses and molded products containing cellulosic fibers. Cellulosic fibers can include digested fibers from softwood (derived from coniferous trees), hardwood (derived from deciduous trees) or cotton linters. Fibers from Esparto grass, bagasse, kemp, flax, and other lignaceous and cellulosic fiber sources may also be utilized.

In some embodiments, the filter paper is Whatman 903. In some embodiments, the filter paper is Ahlstrom grade 226. In some embodiments, the filter paper is Munktell TFN. In some embodiments, the filter paper is Isocode.

In some embodiments, a weak base is sorbed to the filter paper before depositing the filter paper into the vessel. A "weak base" refers to a base which has a pH of about 6 to 10, preferably about pH 8 to 9.5. One function of the weak base may be to act as a buffer to maintain a composition pH of about 6 to 10, preferably about pH 8.0 to 9.5, for example, pH 8.6. Hence, a weak base suitable may, in conjunction with other components, provide a pH of 6 to 10, preferably, about pH 8.0 to 9.5. Weak bases include organic and inorganic bases. Examples of inorganic weak bases include, for example, an alkali metal carbonate, bicarbonate, phosphate or borate (For example, sodium, lithium, or potassium carbonate). Organic weak bases include, for example, trishydroxymethyl amino methane (Tris), ethanolamine, triethanolamine and glycine and alkaline salts of organic acids (for example, trisodium citrate). The weak base may be either a free base or a salt, for example, a carbonate salt.

In some embodiments, a chelating agent is sorbed to the filter paper before depositing the filter paper into the vessel. A "chelating agent" refers to any compound capable of complexing multivalent ions including Group II and Group III multivalent metal ions and transition metal ions (for example, Cu, Fe, Zn, Mn, etc). Ethylene diamine tetraacetic acid (EDTA) is an example of a chelating agent. Chelating agents such as a citrate or oxalate can also be applied to the filter paper.

In some embodiments, a detergent is sorbed to the filter paper before depositing the filter paper into the vessel. "Detergent" includes ionic detergents, preferably anionic detergents. A preferred anionic detergent may have a hydrocarbon moiety, such as an aliphatic or aromatic moiety, and one or more anionic groups. Particularly preferred anionic detergents include sodium dodecyl sulphate (SDS) and sodium lauryl sarcosinate (SLS).

In some embodiments, a weak base, a chelating agent and a detergent are sorbed to the filter paper before depositing the filter paper into the vessel. In some embodiments, the filter paper is FTA™. In some embodiments, a method is provided encompassing providing a filter paper wherein a weak base, a chelating agent and a detergent have been sorbed to the filter; for example, providing FTA™ paper.

A "non-cellulosic fiber" refers to a polymeric material characterized by having hydroxyl groups attached to the polymer backbone, for example glass fibers and synthetic fibers modified with hydroxyl groups. Other fibrous materials include synthetic fibers, such as rayon, polyethylene and polypropylene can also be utilized in combination with natural cellulosic fibers or other fibers containing hydroxyl groups. Mixtures of any of the foregoing fibers may be used.

In some embodiments the solid support is opaque. In other embodiments, the solid support is clear or such that approximately 5%, 10%, 15%, 20%, 25%, 30%, 35%, 40%, 45%, 50%, 55%, 60%, 65%, 70%, 75%, 80%, 85%, 90%, 95%, 98%, 99% or more of the light shined on the solid support passes through it.

Kits

Disclosed herein are kits of components. In some embodiments, the components of the kit encompass a primer and a fluorescently labeled probe with a 5' signaling moiety and a 3' quencher, wherein the probe does not form a stable stem loop structure and the probe is not conjugated with a MGB. In other embodiments, the components of the kit encompass a primer and two or more fluorescently labeled probes with a 5' signaling moiety and a 3' quencher, wherein the probes do not form stable stem loop structures and the probes are not conjugated with a MGB. In some embodiments, the probe or probes detect a multicopy target.

In some embodiments, the components of the kit encompasses at least two primers a fluorescently labeled probe with a 5' signaling moiety and a 3' quencher, wherein the probe does not form a stable stem loop structure and the probe is not conjugated with a MGB. In other embodiments, the components of the kit encompass at least two primers and two or more fluorescently labeled probes with a 5' signaling moiety and a 3' quencher, wherein the probes do not form stable stem loop structures and the probes are not conjugated with a MGB. In some embodiments, two primers of the at least two primers form a primer pair. In other embodiments, the one or more primers are complementary to a sequence flanking a multicopy target locus. In some of the embodiments, none of the probes contained in the kit are conjugated with an MGB. In some of the embodiments, the kit encompasses a plurality of probes and none of the probes contained in the kit are conjugated with an MGB.

In some embodiments, a kit of components is disclosed wherein the kit of components encompasses a multiplicity of primers and a multiplicity of fluorescently labeled probes, wherein each of the probes possesses a 5' signaling moiety and a 3' quencher, wherein each of the probes detects a multicopy locus and wherein each probe is not conjugated with an MGB and wherein each of the multiplicity of primers is complementary to a sequence flanking a multi-copy locus.

In some embodiments, the components of the kit encompass a polymerase.

A stable stem-loop is one with a melting temperature above 40° C., or above 45° C., or above 50° C., or above 55° C., or above 60° C. or above 65° C., or above 70° C., or above 75° C. or above 80° C. or more.

In some embodiments, one or more of the components of the kit are in one or more vessels. In some embodiments, the kit is packaged in a single enclosure, for instance a box. In some embodiments, the reagents are provided in vessels of suitable strength for direct use or use after dilution.

Disclosed herein are compositions, the compositions being the combination of constituents of the methods, and the intermediates of the methods disclosed above or the end product of the methods disclosed above.

Accordingly, in some embodiments a composition is disclosed the composition encompassing a fluorescently labeled probe, a primer and a solid support, wherein the fluorescently labeled probe is not conjugated with an MGB. In some embodiments, the composition encompasses two or more fluorescently labeled probes, two or more primers and a solid support, wherein each of the two or more fluorescently labeled probes are not conjugated with an MGB. In some embodiments, the composition encompasses two or more fluorescently labeled probes, two or more primers and a solid support, wherein the composition does not encompass an MGB. In some embodiments, one or more probes detect a multicopy locus. In some embodiments, the one or more primers flank a multicopy locus.

EXAMPLES

The Effect of Punch Size and Baseline Setting on qrtPCR Quantification

Because illuminating the sample with light and detecting the fluorescence signal is central to a qrtPCR assay the influence of paper punch size on the qrtPCR assay was tested. Punches of various diameters, 0.5 mm, 1 mm and 2 mm were tested in a qrtPCR assay. Individual punches with different diameters were generated from PE-swabs and placed directly into a well of MicroAmp® Optical 96-Well Reaction Plate. Punches were made from negative control PE-swabs; that is, PE-swabs that had not be used to swab a surface. The punches were then subjected to qrtPCR analysis.

To analyze the influence of punches and punch size on qrtPCR, punches of various sizes were deposited in wells of a MicroAmp® Optical 96-Well Reaction Plate. Wells without punches were also analyzed. To each well were added 10.5 µL Quantifiler® Duo Primer Mix, 12.5 µL Quantifiler® Duo PCR reaction mix and 2 µL de-ionized water. Also present in the wells was the IPC template control. Quantification reactions were carried out on Applied Biosystems 7500 Real-Time PCR System using the manufacture recommended protocol. The Applied Biosystems 7500 Real-Time PCR System utilizes a CCD detector. The quantification results were analyzed using SDS Software v2.0.6 (Life Technologies). Results from this analysis are shown in FIG. 1.

Except for the ROX™ passive reference fluorescent channel, the presence of a filter paper punch in the reaction well results in elevated background florescent signal in the FAM™, VIC® and NED™ fluorescent channels. The magnitude of the background elevation is correlated with the size of the filter paper punch in the reaction well. In addition, it was also observed that the background florescent signal increases after each thermal cycle and the rate increase is apparently correlated with the size of the filter paper punch.

The Quantifier® Trio is a recently developed kit for quantifying human DNA in a sample. While the Quantifiler® Duo detects the presence of two human targets, an autosomal target and a Y-chromosome target, the Quantifiler® Trio detects two autosomal targets and a Y-chromosomal target. As described above with the Quantifiler® Duo, the influence of punches and punch size using the Quantifiler® Trio was also tested.

Punches of various diameters, 0.5 mm, 1 mm and 2 mm were made and deposited in wells of a MicroAmp® Optical 96-Well Reaction Plate. Wells without punches were also analyzed. To each well were added 10.5 µL Quantifiler® Trio Primer Mix, 12.5 µL Quantifiler® Trio PCR reaction mix and 2 µL de-ionized water. Also present in the wells was the IPC template control. Quantification reactions were carried out on Applied Biosystems® 7500 Real-Time PCR System using the manufacture recommended protocol. The Applied Biosystems® 7500 Real-Time PCR System utilizes a CCD detector. The quantification results were analyzed using SDS Software v2.0.6 (Life Technologies). Results from this analysis are shown in FIG. 2.

Similar to what observed with the Quantifiler® Duo assay, the presence of a filter paper punch in the reaction well results in elevated background florescent signal in the FAM™ dye and VIC® dye channels. The magnitude of the background elevation appears to be positively correlated with the size of the filter paper punch in the reaction well (FIG. 2). In addition, the background florescent signal slowly increases after each thermal cycle and the rate of the background fluorescent signal increase is also positively correlated to the size of the filter paper punch (FIG. 2).

Minor Groove Binders are Responsible for the Increase in Background Signal

A line of experiments was undertaken to test the role of MGBs in the background fluorescence in direct qrtPCR. Four probes were tested; a probe labeled with FAM™ dye and conjugated with MGB, a probe labeled with FAM™ dye and no MGB, a probe labeled with VIC® dye and conjugated with MGB and a probe labeled with VIC® dye and no MGB.

A 0.5 mm paper disc was deposited in wells of a MicroAmp® Optical 96-Well Reaction Plate. Wells without punches were also analyzed. To each well was added 12.5 µL Quantifiler® Duo or Trio PCR reaction mix and de-ionized water along with one of each of the four primers described above. Also present in the wells was the IPC template control.

Reactions were carried out on Applied Biosystems 7500 Real-Time PCR System using the manufacture recommended protocol. The Applied Biosystems 7500 Real-Time PCR System utilizes a CCD detector. The quantification results were analyzed using SDS Software v2.0.6 (Life Technologies). Results from this analysis are shown in FIG. 3.

As is seen in FIG. 3, background fluorescence does not increase with cycle number with probes without MGBs. In contrast, when an MGB is present, background fluorescence increases with cycle number.

Direct Quantification of Human DNA With and Without MGBs

The experiments above identified MGBs as a source of background in direct quantification assays. These experiments were conducted in the absence of added target and whether the presence of a target would alter the background fluorescence had not been examined. To determine what effect a target would have on background fluorescence and direct quantification a series of experiments were conducted. In these experiments, punches of various diameters, 0.5 mm, 1 mm and 2 mm and 1 ng. of human male DNA were placed into individual wells of MicroAmp® Optical 96-Well Reaction Plate. Wells without punches were also analyzed. To each well were added 8 µL of a probe mix (with or without MGB), 10 µL Quantifiler® Trio PCR reaction mix and 2 µL de-ionized water.

Figure 4A:
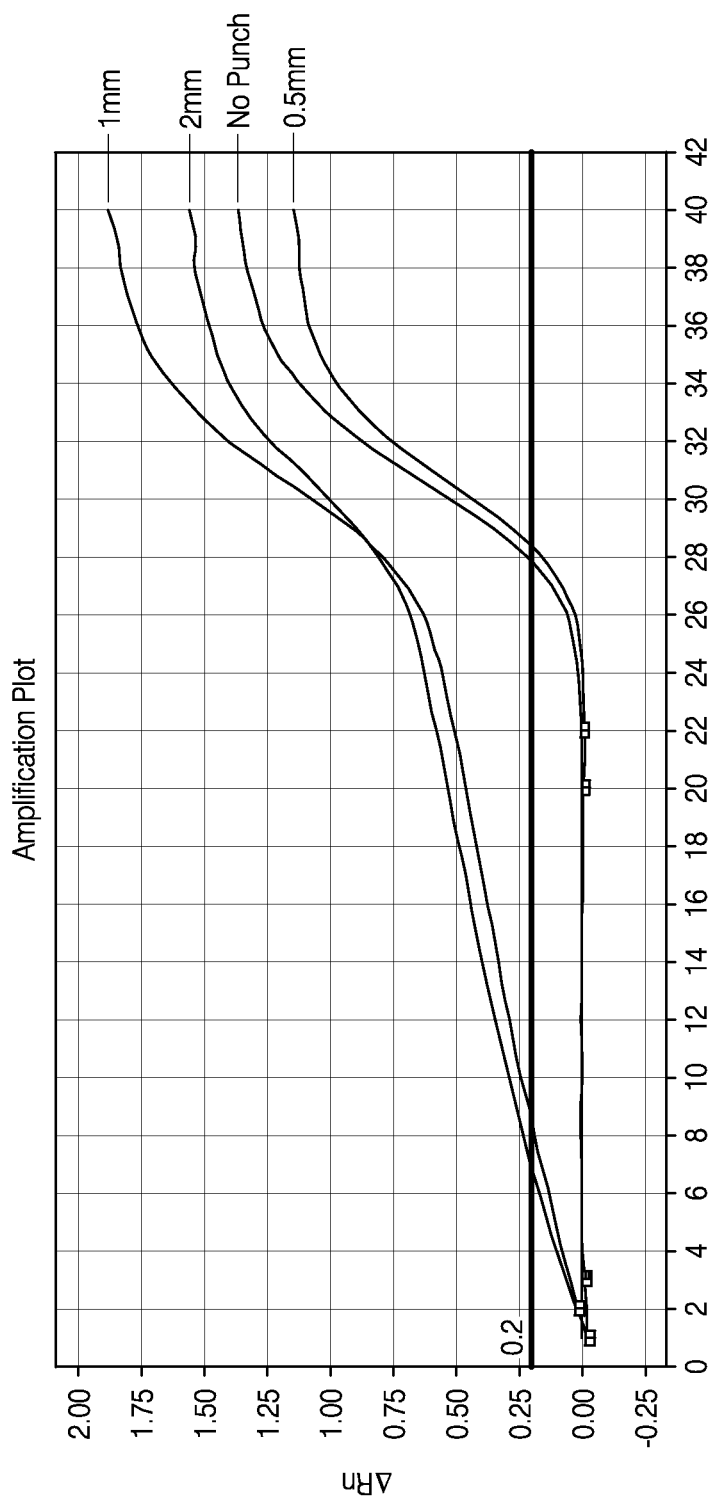
FIGS. 4A, 4B, 4C, and 4D show the results of a qrtPCR assay with 1.0 ng of human male genomic DNA with or without a paper punch (0.5 mm diameter, 1 mm diameter and 2 mm diameter) present in the reaction. Background fluorescence was negligible even when paper punches were present in the reaction when the probes were not conjugated to an MGB.
Figure 4B:
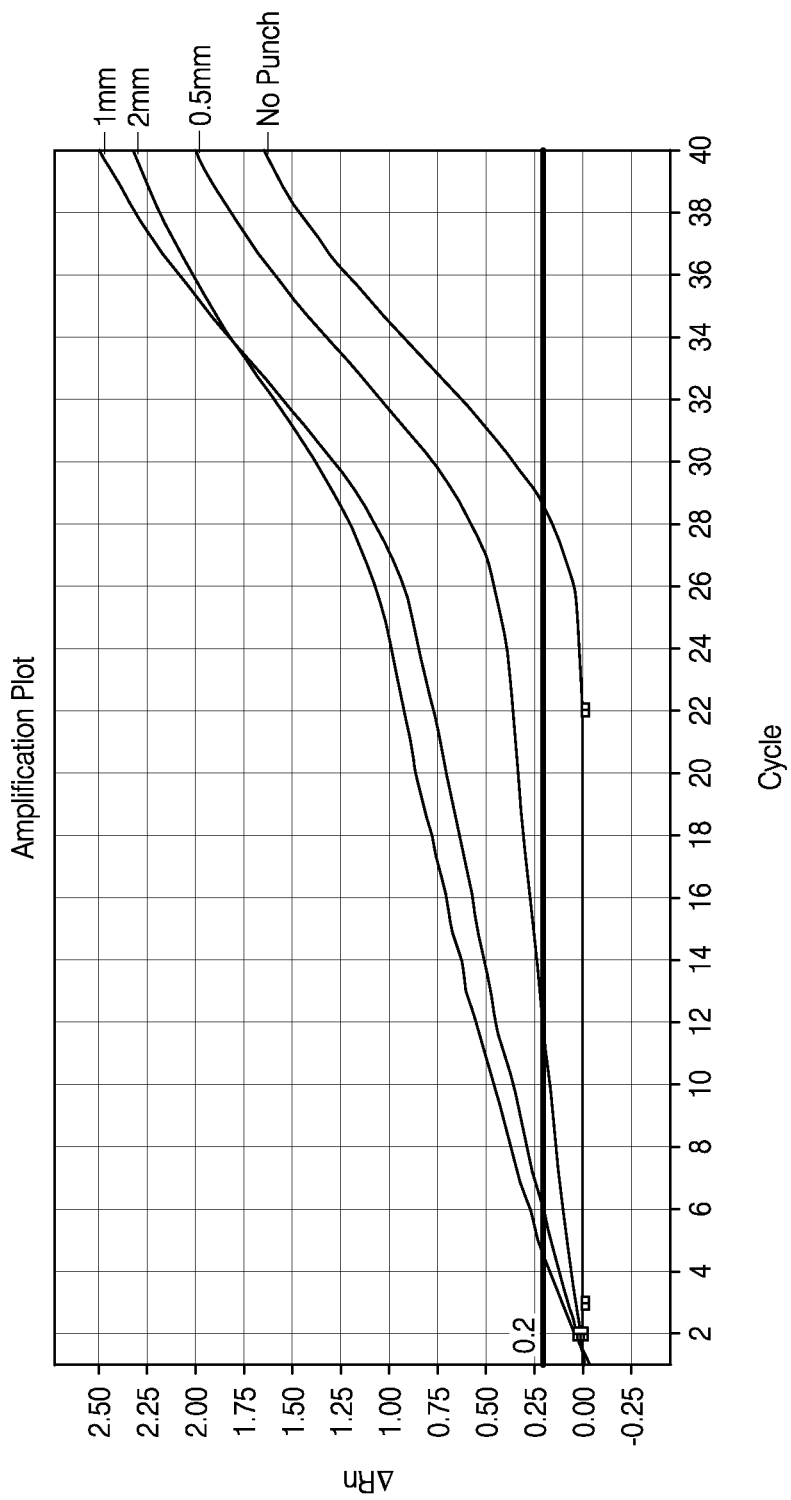
Figure 4C:
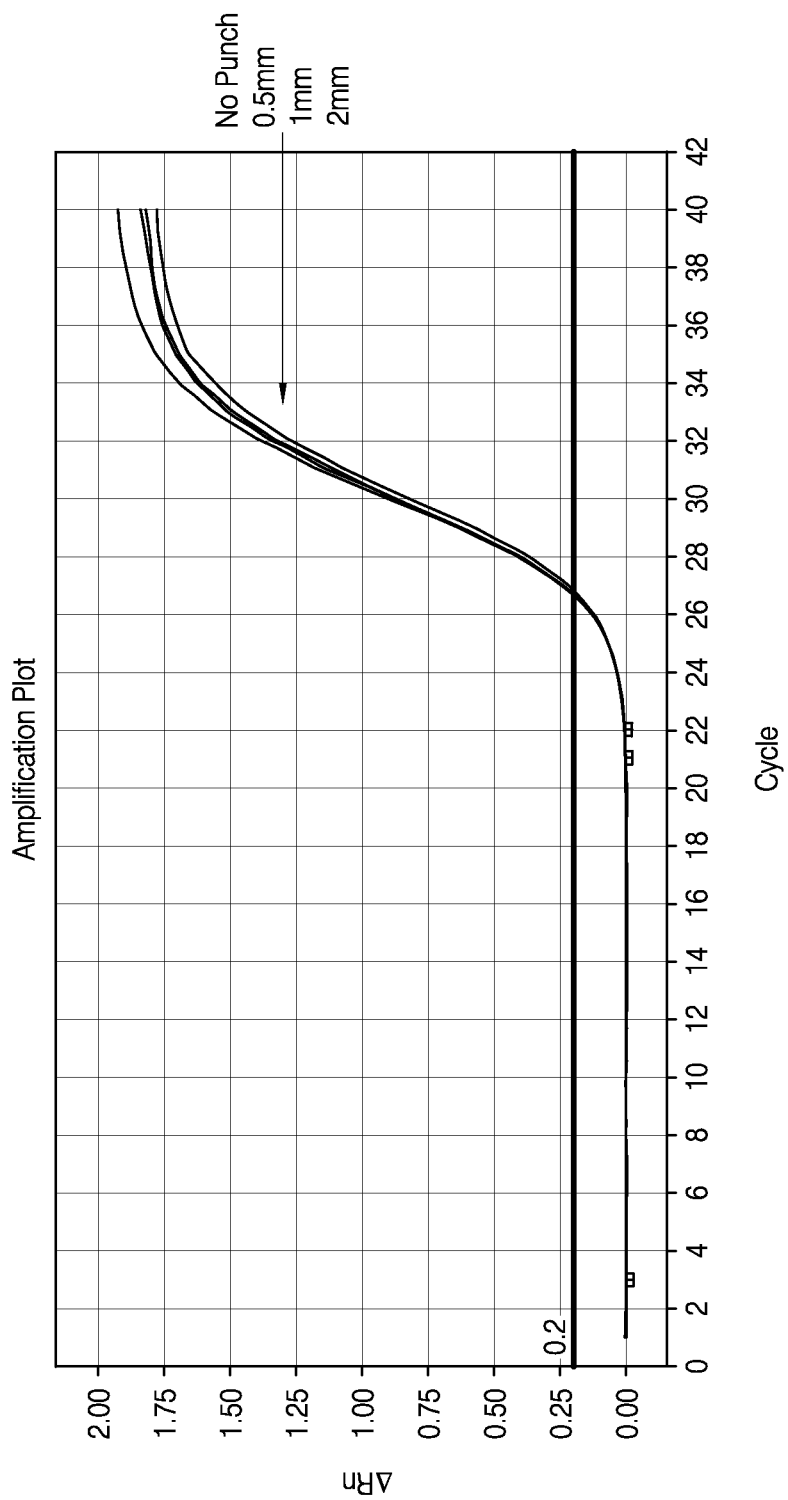
Figure 4D:
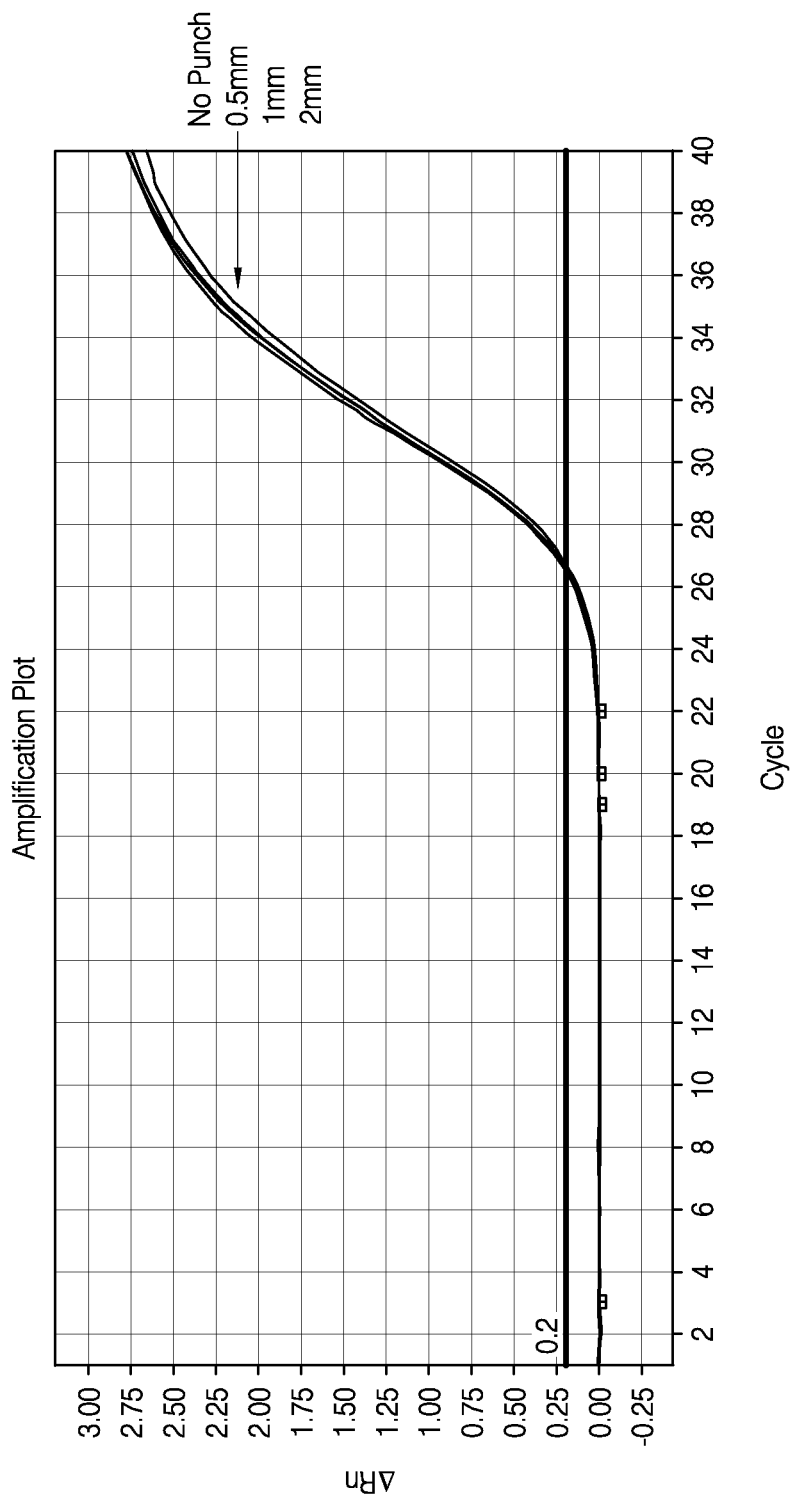

Quantification reactions were carried out on Applied Biosystems® 7500 Real-Time PCR System using the manufacture recommended protocol. The quantification results were analyzed using SDS Software v2.0.6 (Life Technologies). Results from this analysis are shown in FIG. 4. The presence of a 1.0 mm or 2.0 mm paper punch affects the baseline of the amplification plot for the human male target in the presence of MGB (FIG. 4a). All the punch sizes tested affect the baseline for the human autosomal target when the target is detected in the presence of MGB (FIG. 4b). In contrast, paper punch size has little effect when the human male or autosomal target is detected in the absence of MGB (FIGS. 4c and d). These results demonstrate that the presence or absence of template does not alter the finding that the presence of MGBs is responsible for increased background in direct quantification assays.

The Absence of Background Fluorescence is Not Limited to 5'-Exonuclease Probes

The experiments above demonstrate that MGBs are responsible for background fluorescence were performed using 5'-exonuclease probes; a trade name associated with these types of probes is TaqMan®. Another probe type used in qrtPCR assays is a Scorpions® probe. Scorpions® probes have in a 5' to 3' order, a target binding region and a tail comprising a linker and a template binding region. To investigate whether the absence of MGBs and reduced background fluorescence was limited to 5'-exonuclease probes a qrtPCR assay was conducted using Scorpions® probes.

The Qiagen Investigator Quantiplex HYres is a commercially available qrtPCR assay for the quantification of total human DNA and human male DNA. The Quantiplex HYres assay utilizes Scorpions® probes to detect target sequences. The probes used by the Quantiplex HYres assay do not possess MGBs.

Punches of various diameters, 0.5 mm, 1 mm and 2 mm were made and deposited in individual wells of a MicroAmp® Optical 96-Well Reaction Plate. Wells without punches were also included. To these wells was added 9 µl. of the FQ reaction mix, 9 µl. of the IC YQ primer mix and 2 µl. Both the FQ and IC YQ mixes are provide as part of the Investigator Quantiplex HYres assay marketed by Qiagen. 2.5 ng. of human male genomic DNA was added to the wells as template. Wells without template were also included as controls.

Figure 5A:
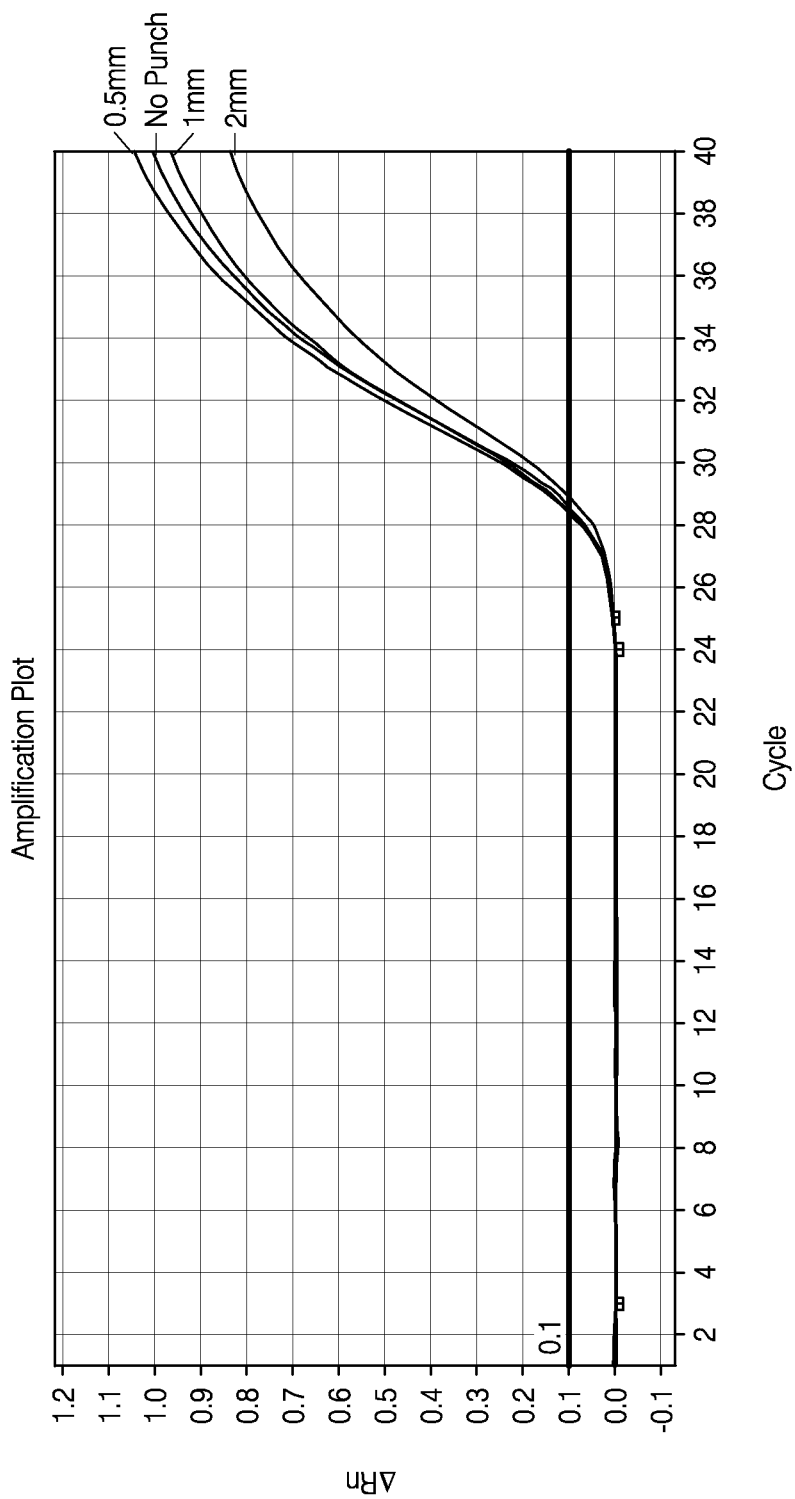
FIGS. 5A and 5B show that reduced background fluorescence is independent of the probe type. 2.5 ng of human male genomic DNA was assayed with the Quantiplex HYres qrtPCR assay. The Quantiplex HYres utilizes Scorpions® probes for target detection. These probes, also without a conjugated MGB, demonstrated little background fluorescence with or without a paper punch (0.5 mm diameter, 1 mm diameter and 2 mm diameter).
Figure 5B:
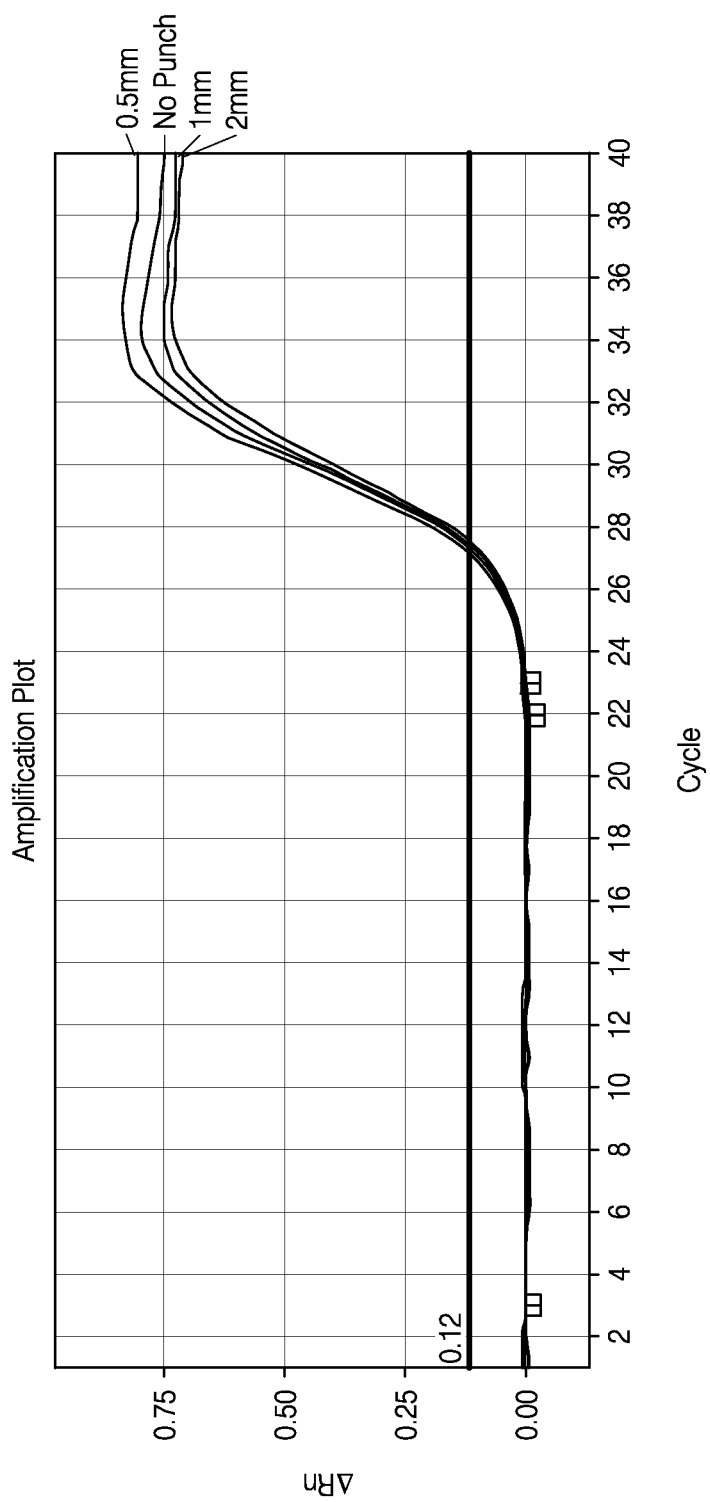

Quantification reactions were carried out on Applied Biosystems® 7500 Real-Time PCR System using the manufacture recommended protocol. The quantification results were analyzed using SDS Software v2.0.6 (Life Technologies). Results from this analysis are shown in FIG. 5. Paper punch size has little effect on the direct quantification of a human autosomal target or Y-chromosome (FIGS. 5a and b). Thus, the presence or absence of increased background is not dependent on probe type but rather the presence or absence of MGBs.

I claim:

1. A method comprising combining a fluorescently labeled probe and a filter paper contacted to a specimen in a reaction vessel, preforming a quantitative real-time polymerase chain reaction (qrtPCR) and detecting a level of fluorescence emanating from the reaction vessel with a charge-coupled device during a thermal cycle while the filter paper is in the reaction vessel, wherein the probe is not conjugated with a minor groove binder and the probe is a reverse complement to a target nucleic acid from a virus and the specimen is not urine.

2. The method of claim 1, wherein the probe is a 5'-exonuclease probe.

3. The method of claim 1, wherein the probe is self-complementary.

4. The method of claim 3, wherein the probe forms a stem-loop structure.

5. A method comprising combining a fluorescently labeled probe and a filter paper contacted to a specimen in a reaction vessel, performing a quantitative real-time polymerase chain reaction (qrtPCR) and detecting a level of fluorescence emanating from the reaction vessel with a charge coupled device during a thermal cycle while the paper is in the reaction vessel, wherein the probe is not conjugated with a minor groove binder and the probe is a reverse complement to a target nucleic acid from a virus and the specimen is not from a child less than a month old.

6. The method of claim 1, further comprising drying the specimen on the filter paper, excising a portion of the filter paper to form a dried excised filter paper, depositing the dried excised filter paper in the reaction vessel, the dried excised filter paper not being contacted to a liquid until the qrtPCR assay.

7. The method of claim 1, wherein a linear scale graph of the level of fluorescence emanating from the reaction vessel as expressed as ΔRn versus cycle number produces a sigmoid curve.

8. The method of claim 5, further comprising drying the specimen on the filter paper, excising a portion of the filter paper to form a dried excised filter paper, depositing the dried excised filter paper in the reaction vessel, the dried excised filter paper not being contacted to a liquid until the qrtPCR assay.

9. The method of claim 5, wherein a linear scale graph of the level of fluorescence emanating from the reaction vessel as expressed as ΔRn versus cycle number produces a sigmoid curve.

* * * * *